US012640262B2

(12) United States Patent
Burgess et al.

(10) Patent No.: US 12,640,262 B2
(45) Date of Patent: May 26, 2026

(54) PATIENT SAFETY DEVICE MAINTENANCE SYSTEM

(71) Applicant: CareFusion 303, Inc., San Diego, CA (US)

(72) Inventors: Brendan John Burgess, San Diego, CA (US); Daniel Abal, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 155 days.

(21) Appl. No.: 18/724,523

(22) PCT Filed: Dec. 29, 2021

(86) PCT No.: PCT/US2021/065546
§ 371 (c)(1),
(2) Date: Jun. 26, 2024

(87) PCT Pub. No.: WO2023/129155
PCT Pub. Date: Jul. 6, 2023

(65) Prior Publication Data
US 2025/0285747 A1     Sep. 11, 2025

(51) Int. Cl.
*G16H 40/40*          (2018.01)
*A61M 5/142*          (2006.01)

(52) U.S. Cl.
CPC ............ *G16H 40/40* (2018.01); *A61M 5/142* (2013.01)

(58) Field of Classification Search
CPC ....... G16H 40/40; G16H 20/17; A61M 5/142; A61M 5/14232; A61M 5/16827;
(Continued)

(56)                References Cited

U.S. PATENT DOCUMENTS

2002/0038392 A1     3/2002   De La Huerga
2012/0062387 A1     3/2012   Vik et al.
(Continued)

FOREIGN PATENT DOCUMENTS

WO        WO-99/62403 A1     12/1999
WO        WO-2015077320 A1 *   5/2015     ............. G16H 20/17
(Continued)

OTHER PUBLICATIONS

A. Drumea and A. Vasile, "Infusion pump medical system controlled with modern system on chip devices," 2006 29th International Spring Seminar on Electronics Technology, St. Marienthal, Germany, 2006, pp. 382-385, doi: 10.1109/ISSE.2006.365134.), (Year: 2006).*

*Primary Examiner* — Linh Giang Le
(74) *Attorney, Agent, or Firm* — Mintz Levin Cohn Ferris Glovsky and Popeo, P.C.

(57)                ABSTRACT

A method may include receiving, from a safety system coupled to an infusion system, repair data associated with a repair event, during which a user accesses the infusion system. The method may also include detecting, based on the repair data, the repair event is unauthorized. The method may also include causing, based on the detecting, at least one safety adjustment to operation of the infusion system. Related methods and articles of manufacture, including apparatuses and computer program products, are also disclosed.

20 Claims, 12 Drawing Sheets

(58) Field of Classification Search
      CPC ...... A61M 2205/18; A61M 2205/3561; A61M
                        2205/505; A61M 2205/52; G05B
                  2219/24001; G05B 2219/24019; G05B
                  19/042; H04L 63/1416; H04L 63/145;
                        H04L 63/0861; H04L 63/1425
      See application file for complete search history.

(56)                      References Cited

U.S. PATENT DOCUMENTS

| | | | |
|---|---|---|---|
| 2012/0185636 A1* | 7/2012 | Leon ..................... | H01L 23/576 |
| | | | 711/E12.001 |
| 2012/0187815 A1 | 7/2012 | Weber et al. | |
| 2014/0276424 A1 | 9/2014 | Davis et al. | |
| 2017/0046806 A1 | 2/2017 | Haldenby et al. | |
| 2017/0111175 A1 | 4/2017 | Oberhauser et al. | |
| 2021/0103883 A1 | 4/2021 | Chappell et al. | |

FOREIGN PATENT DOCUMENTS

| | | |
|---|---|---|
| WO | WO-2019/099568 A1 | 5/2019 |
| WO | WO-2021/108286 A1 | 6/2021 |
| WO | WO-2021/243068 A1 | 12/2021 |

* cited by examiner

400

402

START

ACTIVATE SENSOR FOR REPAIR EVENT DETECTION AT INFUSION SYSTEM

404

COLLECT REPAIR DATA FOR THE REPAIR EVENT

406

REPAIR EVENT COMPLETE?     NO

YES

408

NO     REPAIR EVENT AUTHORIZED?     YES

410

RECORD UNAUTHORIZED REPAIR FOR INFUSION SYSTEM

412

RECORD AUTHORIZED REPAIR FOR INFUSION SYSTEM

END

450

452

454

456

458

PATIENT SAFETY DEVICE MAINTENANCE SYSTEM

CROSS REFERENCE TO RELATED APPLICATION

This application is a national stage filing under 35 U.S.C. § 371 of International Application No. PCT/US2021/065546 filed Dec. 29, 2021, and entitled "PATIENT SAFETY DEVICE MAINTENANCE SYSTEM" the contents of which is hereby incorporated by reference herein in its entirety.

TECHNICAL FIELD

The subject matter described herein relates generally to a device maintenance system and more specifically to a patient safety device maintenance system for a medical device such as an infusion system.

BACKGROUND

Infusion devices, such as infusion pump systems, can include a complicated arrangement of components. Repairing and/or maintaining the infusion devices can be difficult. Also, an improperly repaired and/or assembled infusion device may render the device unusable or cause injury to a patient. Thus, maintenance personnel or other users who perform maintenance or repairs on the infusion devices should be qualified, trained, and/or certified to ensure the infusion devices are assembled or repaired properly. However, it can be difficult to ensure that only authorized personnel make repairs and/or perform maintenance on the infusion devices, and to track both authorized and unauthorized repairs and/or maintenance. Furthermore, it can be difficult to prevent and/or track unauthorized repairs or use of unauthorized replacement parts, which can similarly render the infusion devices unusable, damage components of the infusion devices, or lead to injury to the patient.

SUMMARY

Systems, methods, and articles of manufacture, including computer program products, are provided for a patient safety device maintenance system for an infusion system. The patient safety device maintenance system consistent with implementations of the current subject matter may assist with tracking maintenance of a medical device (e.g., an infusion system) and adjust the medical device in response to detection of an unauthorized access of the medical device.

According to some aspects, a method includes receiving, from a safety system coupled to an infusion system, repair data associated with a repair event, during which an element within a housing of the infusion system is accessed. The method may also include detecting, based on the repair data, the repair event is unauthorized. The method may also include causing, based on the detecting, at least one safety adjustment to operation of the infusion system.

In some aspects, the repair event includes one or more of a repair of the element of the infusion system, a replacement of the element of the infusion system, opening the housing, and a maintenance performed on the infusion system.

In some aspects, the infusion system includes an infusion pump.

In some aspects, the infusion system includes: an infusion pump, and a control device coupled to the infusion pump. The control device includes at least one data processor and at least one memory storing instructions which, when executed by the at least one data processor, control operation of the infusion pump.

In some aspects, the safety system includes a tamper switch. The tamper switch includes: at least two electrically conductive surfaces of the infusion system. Contact between the at least two electrically conductive surfaces forms a circuit. The tamper switch may also include a fastener configured to maintain contact between the at least two electrically conductive surfaces. Removal of the fastener is configured to allow access to the infusion system during the repair event. Removal of the fastener is further configured to activate the tamper switch.

In some aspects, the safety system further includes the housing of the infusion system. The housing defines at least one of the at least two electrically conductive surfaces.

In some aspects, the repair data includes information indicating activation of the tamper switch. The detecting includes determining the repair event is unauthorized when the tamper switch is activated.

In some aspects, the safety system includes a damage switch configured to indicate the infusion system should be accessed during the repair event.

In some aspects, the damage switch includes one or more of a moisture sensor configured to be activated upon detecting an ingress of fluid into an interior of the infusion system and an accelerometer configured to be activated upon detecting an acceleration indicating an impact on the infusion system.

In some aspects, the repair data includes information indicating activation of one or more of the moisture sensor and the accelerometer.

In some aspects, the safety system includes: a supervisor chip coupled to the infusion system, a primary switch coupled to the supervisor chip and to the infusion system, and a secondary switch coupled to the supervisor chip and to the infusion system.

In some aspects, the primary switch includes the tamper switch, and the secondary switch includes the damage switch.

In some aspects, the repair data includes information indicating activation of one or more of the primary switch and the secondary switch.

In some aspects, the at least one safety adjustment includes recording, by the supervisor chip, a timestamp associated with the activation of the one or more of the primary switch and the secondary switch.

In some aspects, the at least one safety adjustment includes erasing a security value from memory of the supervisor chip, thereby limiting use of the infusion system.

In some aspects, the method includes resetting the security value upon receipt of a selection from an authorized user, thereby restoring the use of the infusion system.

In some aspects, the safety system includes a tamper evident data tag. The repair data includes no detection of the tamper evident data tag, and the detecting includes determining the repair event is unauthorized based on the no detection of the tamper evident data tag.

In some aspects, the safety system includes a light sensor and/or switch within a housing of the infusion system. The repair data includes a scan of a memory coupled to the light sensor and/or switch to determine whether an event indicating the light sensor and/or switch was triggered is stored in the memory. The light sensor and/or switch may be triggered when the housing is removed from the infusion system, and the detecting includes determining the repair event is unauthorized based on a determination that the event is stored in the memory.

In some aspects, the safety system includes a camera coupled to the housing of the infusion system. The repair data includes a light level in a field of view of the camera. The detecting includes determining the repair event is unauthorized based on the light level in the field of view of the camera corresponding to a light level threshold.

In some aspects, the safety system includes a drop sensor coupled to the infusion system. The repair data includes a pattern of movement reflecting a repair of the infusion system, and the detecting includes determining the repair event is unauthorized based on the pattern of movement.

In some aspects, the system include an authorized user registry, and the repair data includes user data associated with the infusion system during the repair event. Determining the repair event is unauthorized includes determining that the user data is unassociated with a user included in the authorized user registry.

In some aspects, the system an authorized user registry, and the repair data includes user data associated with the infusion system during the repair event. Determining the repair event is unauthorized includes determining that the user data is associated with a user authorized to perform a different repair event than the repair event in the authorized user registry.

In some aspects, the unauthorized user is one or more of unqualified, not trained, and not certified.

In some aspects, the safety system includes a location sensor coupled to the infusion system. The repair event is unauthorized when the repair event is performed in an unauthorized location detected by the location sensor.

In some aspects, the at least one safety adjustment includes a transmission of one or more of a visual alert, an audio alert, an audiovisual alert, and a tactile alert.

In some aspects, the audio alert includes one or more of a periodic noise and an audio file indicating the infusion system was repaired by an unauthorized user.

In some aspects, the at least one safety adjustment includes a display of an indication via a user interface coupled to the infusion pump. The indication indicates the infusion system was repaired by an unauthorized user.

In some aspects, the at least one safety adjustment includes a display of an indication via a user interface coupled to the infusion pump. The indication includes at least one of a banner and a persistent and perceivable indicator.

In some aspects, the at least one safety adjustment includes disabling network connectivity in the infusion system.

In some aspects, the at least one safety adjustment includes transmission, to a device management server coupled to the infusion system, of a message indicating the repair event was unauthorized.

In some aspects, the at least one safety adjustment includes creation, in a distributed ledger, of an entry includes an identifier associated with the infusion system and a timestamp of the repair event.

In some aspects, the distributed ledger is a blockchain ledger.

In some aspects, the entry further includes an identifier associated with the user.

In some aspects, the at least one safety adjustment includes storage of a security value in a secure register of the infusion system. The security value indicates one or more of the detecting and a timestamp of the repair event.

In some aspects, the user includes one or more of a manufacturer, a repair personnel, a clinician, and a patient.

According to some aspects, an infusion system includes: a supervisor chip, a primary switch coupled to the supervisor chip, a secondary switch coupled to the supervisor chip, and a controller including at least one data processor and a memory for storing instructions, which when executed by the at least one data processor, result in operations. The operations include recording, by the supervisor chip, a timestamp associated with activation of the one or more of the primary switch and the secondary switch. The activation indicates unauthorized access of the infusion system.

In some aspects, the operations include erasing a security value from memory of the supervisor chip, thereby preventing use of the infusion system.

In some aspects, the operations further include: resetting the security value upon receipt of a selection from an authorized user, thereby allowing the use of the infusion system.

In some aspects, the primary switch is a tamper switch includes: at least two electrically conductive surfaces. Contact between the at least two electrically conductive surfaces forms a circuit. The tamper switch may also include a fastener configured to maintain contact between the at least two electrically conductive surfaces. Removal of the fastener is configured to allow access to the infusion system. Removal of the fastener is further configured to activate the tamper switch.

In some aspects, the safety system further includes a housing of the infusion system. The housing defines at least one of the at least two electrically conductive surfaces.

In some aspects, the operations include determining the access to the infusion system is unauthorized when the tamper switch is activated.

In some aspects, the secondary switch is a damage switch configured to indicate the infusion system should be accessed.

In some aspects, the damage switch includes one or more of a moisture sensor configured to be activated upon detecting an unwanted ingress of fluid into an interior of the infusion system and an accelerometer configured to be activated upon detecting an acceleration indicating an impact on the infusion system.

Implementations of the current subject matter can include methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including, for example, to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to a patient safety device maintenance system, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
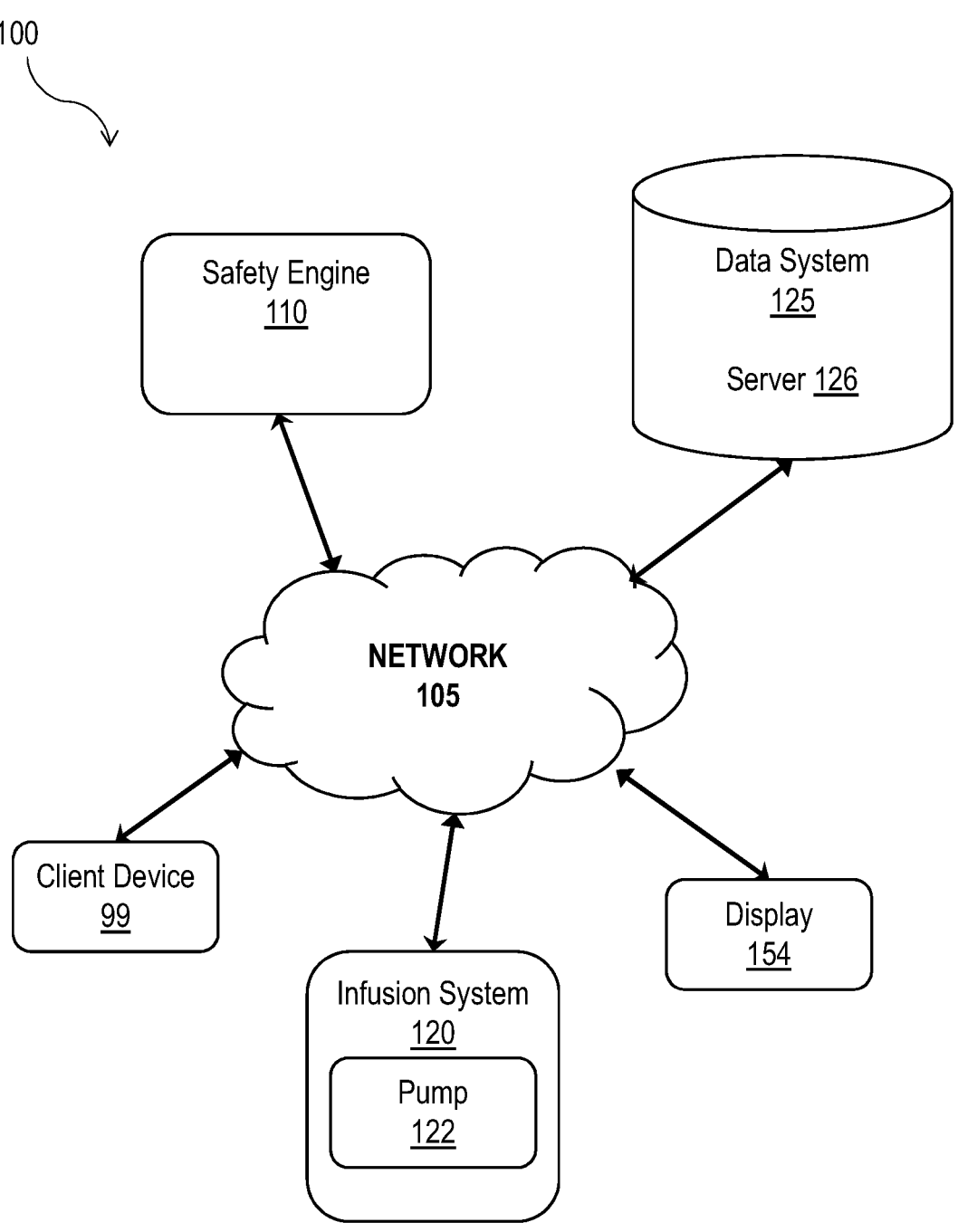
FIG. 1 depicts a system diagram illustrating a patient safety device maintenance system, in accordance with some example implementations.

Infusion devices, such as infusion pump systems, can include a complicated arrangement of components. Repairing and/or maintaining the infusion devices can be difficult. Thus, maintenance personnel or other users who perform maintenance or repairs on the infusion devices should be qualified, trained, and/or certified to ensure the infusion devices are assembled or repaired properly. However, in many instances, patients or other users (e.g., medical facilities, medical personnel, and/or the like) may choose to repair the infusion devices on their own or by using an unauthorized third party. Using an unauthorized third party or improperly repairing the device may render the device unusable or lead to an injury to a patient using the device.

As an example, some infusion devices require specialized equipment and fixtures to repair the devices and/or perform maintenance on the devices. For example, an infusion device may include a series of springs to control occluders, and/or the like. To repair such an infusion device, a fixture may be used to hold the series of springs in place when a housing of the infusion device is removed, and one or more components of the infusion device are repaired and/or replaced. If the fixture is not used, the springs or other components may become loose or become bent, resulting in jamming of the springs and/or complete failure of the infusion device. Both instances can lead to injury to the patient due to the infusion device malfunctioning as a result of the improperly assembled and/or damaged infusion device.

The patient safety device maintenance system consistent with implementations of the current subject matter helps to prevent, limit, or track such issues. For example, the patient safety device maintenance system consistent with implementations of the current subject matter helps to detect when an infusion device has been modified by an unauthorized user and, upon detection of the unauthorized use, make one or more safety adjustments at the infusion device to protect patient and clinical safety. Thus, the patient safety device maintenance system may protect the integrity of the infusion device and help to ensure safe operation of the infusion device.

In some instances, manufacturers of the infusion devices may authorize certain authorized users or third parties to make repairs and/or perform maintenance on the infusion devices. As noted above, the maintenance personnel who perform maintenance or repairs on the infusion devices may be qualified (e.g., trained, and/or certified) to ensure the infusion devices are assembled or repaired properly in a manner that meets or exceeds the required quality standards. However, it may be difficult to ensure that the maintenance personnel performing the maintenance or repairs is actually qualified. The patient safety device maintenance system consistent with implementations of the current subject matter helps to track the personnel (authorized and/or unauthorized) performing the maintenance and/or repairs on the infusion devices. Additionally or alternatively, the patient safety device maintenance system consistent with implementations of the current subject matter helps to ensure that only qualified personnel (e.g., authorized users) are able to perform maintenance and/or repairs on the infusion devices.

Furthermore, unauthorized replacement parts can cause critical failure of the infusion devices and/or cause the infusion devices to operate in a way that is harmful to the patient using the infusion devices. As an example, unauthorized keypads can significantly impact operation of the infusion devices and control over the delivery of medication to the patient using the infusion devices. As another example, unauthorized batteries or other materials may not be subjected to rigid quality control procedures before being implemented in the infusion devices, possible leading to damage to the infusion devices and/or harm to the patient.

Despite the potential harms associated with using an unauthorized replacement part in an infusion device and/or an unauthorized repair of the infusion device, it can be difficult to prevent and/or track unauthorized repairs or use of unauthorized replacement parts. To determine whether the infusion devices have been opened or repaired, some infusion devices employ paint or other markers to seal the device. However, such paint or markers can be easily faked and/or broken. Infusion devices also generally do not have mechanisms for tracking the use of replacement parts and/or maintenance performed on the infusion devices. Thus, it can be difficult to ensure that only authorized personnel make repairs and that those personnel only use authorized replacement parts. The patient safety device maintenance system consistent with implementations of the current subject matter helps to determine when an infusion device has been accessed, and to track the access of the infusion device. The patient safety device maintenance system may also perform one or more safety adjustments to the operation of the infusion device to improve the safety of the patient and to help prevent future unauthorized access of the infusion device.

FIG. 1 depicts a system diagram illustrating a patient safety device maintenance system 100, consistent with implementations of the current subject matter. Referring to FIG. 1, the patient safety device maintenance system 100 may include a safety engine 110, an infusion system 120, a display 154, a client device 99, and a data system 125. The safety engine 110, the display 154, and/or the data system 125 may form a portion of the infusion system 120 and/or may be positioned within a housing (e.g., a housing 270) of the infusion system 120.

The infusion system 120 may include a pump 122 (also referred to herein as an "infusion device"). Additionally or alternatively, the infusion system 120 may include a pump control device coupled to and/or forming a part of the pump 122. The pump control device may include at least one processor and at least one memory for storing instructions, which when executed by the at least one processor cause the pump 122 to perform one or more operations, such as to deliver a medication to a patient. The pump 122 may be a TCI pump, a syringe pump, an anesthesia delivery pump, a patient-controlled analgesic (PCA) pump, a large volume pump (LVP), a small volume pump (SVP), an ambulatory pump, and/or the like, and may be configured to deliver a medication to a patient. However, it should be appreciated that the pump 122 may be any infusion device configured to deliver a substance (e.g., fluid, nutrients, medication, and/or the like) to a patient's circulatory system or epidural space via, for example, intravenous infusion, subcutaneous infusion, arterial infusion, epidural infusion, and/or the like. Alternatively, the pump 122 may be an infusion device configured to deliver a substance (e.g., fluid, nutrients, medication, and/or the like) to a patient's digestive system via a nasogastric tube (NG), a percutaneous endoscopic gastrostomy tube (PEG), nasojejunal tube (NJ), and/or the like. Moreover, the pump 122 may be part of a patient care system (e.g., a patient care system 20) that includes one or more additional pumps.

The display 154 may form a part of the infusion system 120 (e.g., the pump 122) or may be separately coupled as part of a client device 99. The display 154 may also include a user interface. The user interface may form a part of a display screen of the display 154 that presents information to a user and/or the user interface may be separate from the display screen. For example, the user interface may be one or more buttons, or portions of the display screen that is configured to receive an entry from the user. As described herein, the display 154 may additionally or alternatively display one or more alerts or other information associated with a repair event, during which a user may access the infusion system 120 (e.g., the pump 122) to repair, replace, maintain, check, update, or clean one or more elements (e.g., device elements such as parts, components, or the like) of the system 120. The access during the repair event may be virtual such as to update or maintain firmware of the device or the access may be physical such as to open the housing of the infusion system 120 to perform work on a battery or other element in the housing. The repair event is generally performed while the infusion system 120 is unassociated with a patient or specific infusion order.

The client device 99 may be a mobile device such as, for example, a smartphone, a tablet computer, a wearable apparatus, and/or the like. However, it should be appreciated that the client device 99 may be any processor-based device including, for example, a desktop computer, a laptop computer, a workstation, and/or the like. For example, via the client device 99, the user may be able to configure certain parameters of the pump 122, such as an air in line threshold, a rate limit, an alarm limit, and the like. Additionally, in some examples, via the client device 99, the user may configure various drug protocols with default settings and safety parameters (e.g., setting a limit to a dose of a drug).

The data system 125 may include one or more databases, providing physical data storage within a dedicated facility and/or being locally stored on the pump 122 and/or the display 154. The data system 125 may include an inventory system, a patient care system, an administrative system, an electronic medical record system, and/or the like, which store a plurality of electronic medical records, each of which include the patient's medical history, one or more fluid delivery protocols, and/or the like. Additionally and/or alternatively, the data system 125 may include cloud-based systems providing remote storage of data in, for example, a multi-tenant computing environment and/or the like. The data system 125 may also include non-transitory computer readable media.

In some implementations, the data system 125 may include and/or be coupled to a server 126 (e.g., a device management server), which may be a server coupled to a network, a cloud server, and/or the like. The client device 99 may wirelessly communicate with the server 126. The server 126 may communicate directly with the pump 122, with the pump 122 via the safety engine 110, and/or through the client device 99 and/or the display 154. The server 126, which may include a cloud-based server, may provide data and/or instructions from the data system 125 to the pump 122 and/or the safety engine 110, the client 99, or the display 154 to be transmitted to the pump 122. Additionally or alternatively, the server 126 may receive data, such as repair data (e.g., data associated with a repair event, during which a user accesses the infusion system 120, such as the pump 122) from the pump 122 and/or the safety engine 110. The data system 125 may include an authorized user registry. The authorized user registry may include user data that identifies users and permissions for performing repair events. The registry may include a binary list of users that are authorized. The registry may include a binary list of users that are unauthorized. The registry may associate specific users with specific repair events (e.g., battery replacement, door replacement, software upgrade), devices (e.g., pump model, brand, version, type, etc.), or device elements (e.g., battery, housing, pump module, etc.). The registry may be indexed by user identifier to expedite the identification of appropriate registry entries for a specific user.

The safety engine 110, the pump 122, the display 154, the client device 99, and/or the data system 125 may be communicatively coupled via a network 105. Meanwhile, the network 105 may be any wired and/or wireless network including, for example, a public land mobile network (PLMN), a local area network (LAN), a virtual local area network (VLAN), a wide area network (WAN), the Internet, and/or the like.

The safety engine 110, which may define a controller, may include at least one processor and/or at least one memory for storing instructions, which when executed by the at least one processor performs one or more operations to, for example, improve a safety of a patient and/or track access of the infusion system 120 (e.g., the pump 122). The safety engine 110 may form a part of and/or be coupled to the pump 122.

In some implementations, the safety engine 110 receives repair data from a safety system 204 (see FIG. 2) of the infusion system 120 (e.g., the pump 122). The repair data may include data associated with a repair event, during which a user accesses the infusion system 120. The user includes one or more of a patient, a clinician, a device manufacturer, a repair personnel, and/or the like. The user accesses the infusion system 120, such as the pump 122 during a repair event that includes one or more of a repair of an element (e.g., device elements such as parts, components, or the like) of the infusion system 120, maintenance performed on the infusion system 120, cleaning of the infusion system 120, performing a mechanical check on the infusion system 120, and/or the like. For example, during the repair event, the user may open the pump 122, remove the housing 270 of the pump 122, and/or remove one or more other components of the pump 122.

The user accessing the infusion system 120 should be authorized as an authorized user. In other words, the user accessing the infusion system 120 should be trained and/or certified for making repairs and/or performing maintenance on the infusion system 120. If the user is not authorized (e.g., is an unauthorized user), the user may not properly repair the infusion system, perform maintenance on the infusion system 120, use the infusion system 120, and/or the like, which may lead to failure of the infusion system 120 and/or harm to the patient using the infusion system 120.

To improve the safety of the patient, the patient safety device maintenance system 100 (e.g., via the safety engine 110) may detect when an unauthorized user accesses the infusion system and/or when a user uses an unauthorized component during the access of the infusion system. For example, the safety engine 110 may detect the repair event is unauthorized based on the repair data received from the safety system 204. The repair event is unauthorized when the unauthorized user accesses the infusion system 120 and/or uses an unauthorized component in the infusion system 120.

In some implementations, when the safety engine 110 determines that the repair event is unauthorized, the safety engine 110 may cause at least one safety adjustment to operation of the infusion system 120. The safety adjustment may include transmission of an alert, storage of information associated with the repair event, transmission of an alarm, disablement of the infusion system 120, changing an operation of the infusion system 120, and/or the like. Thus, the safety engine 110 may track access of the infusion system 120 for later auditing and/or investigation, and in some instances, may prevent use of the infusion system 120 until the infusion system 120 is evaluated by an authorized user.

For example, the safety adjustment may include transmission of one or more of a visual alert, an audio alert, an audio visual alert, a tactile alert, and/or another alert. The audio alert may include a periodic noise and/or an audio file indicating the infusion system was repaired and/or accessed by an unauthorized user. The safety adjustment may additionally or alternatively include a display of an indication, via a user interface (e.g., of the display 154 and/or a display 236), indicating the infusion system was accessed by an unauthorized user. The safety adjustment may additionally or alternatively include a display of an indication including at least one banner or persistent and perceivable indicator. The safety adjustment may additionally or alternatively include disabling network connectivity in the infusion system 120. The safety adjustment may additionally or alternatively include transmission (e.g., to the safety engine 110 or directly to the server 126), of a message indicating the repair event was authorized and/or unauthorized. The safety adjustment may additionally or alternatively include creation, in a distributed ledger (e.g., a blockchain ledger) of the infusion system 120, of an entry including an identifier associated with the infusion system, a timestamp of the repair event, and/or an identifier associated with the user accessing the infusion system 120. The safety adjustment may additionally or alternatively include storage of a security value in a secure register of the infusion system indicating the detection of the unauthorized repair event and/or a timestamp associated with the repair event.

Figure 2:
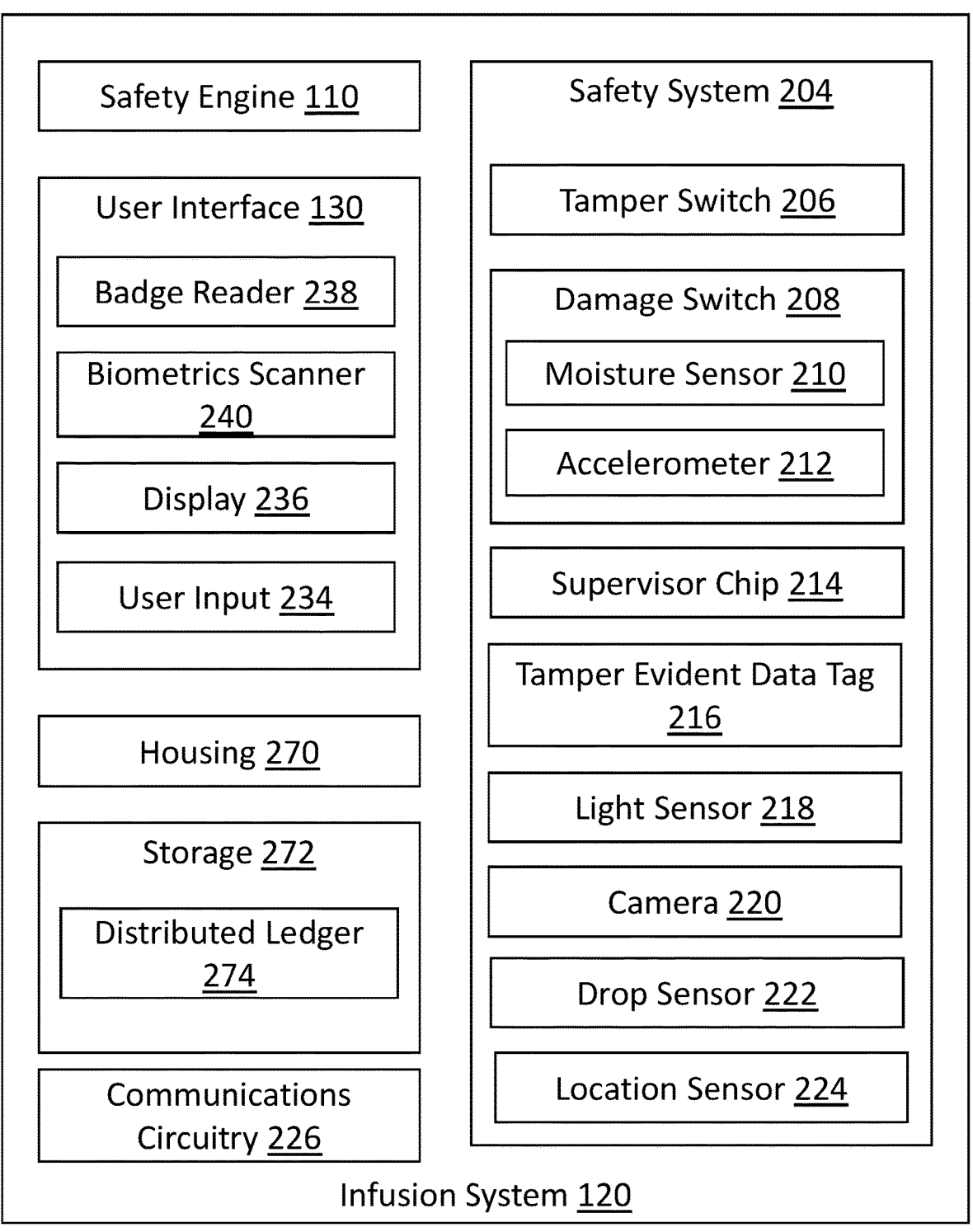
FIG. 2 schematically depicts an example infusion system, in accordance with some example implementations.

FIG. 2 schematically depicts an example of the infusion system 120 (e.g., the pump 122), consistent with implementations of the current subject matter. As shown in FIG. 2, the infusion system 120 may include the safety engine 110, a housing 270, a user interface 130, a data storage 272 (which may be the same as and/or include the data system 125), a safety system 204, and communications circuitry 226. While the infusion system 120 is described as including the safety system 204, the safety engine 110, the user interface 130, the housing 270, the communications circuitry 226, and the storage 272, it should be appreciated that the safety system 204, the safety engine 110, the user interface 130, the housing 270, the communications circuitry 226, and the storage 272 may be implemented in one or more other medical devices or medical systems, such as a medication preparation station, medication dispensing stations, flow cytometers, and other medical instruments.

Referring to FIG. 2, the user interface 130 may include a badge reader 238, a biometrics scanner 240, a display 236, a user input 234, and/or the like. The user interface 130 may be coupled to or integrated with the pump 122. In some implementations, at least a portion of the user interface 130 forms a part of the pump 122, and at least a portion of the user interface 130 is coupled to an external client device, such as a computer, mobile phone, and/or the like, which is communicatively coupled to the pump 122. In some implementations, the user interface 130 forms a part of, includes, and/or is coupled to the display 154.

The user interface 130 may receive data that is used for a later audit of the repair events at the pump 122. For example, the pump 122 may include one or more auditing features. The one or more auditing features may be features that allow for the repair events to be tracked and associated with a user, such as the user accessing the pump 122. For example, the pump 122 may record information collected when the pump 122 is accessed, including the identification tag (barcode, RFID tag, etc.) of the user and/or the identity of the user who accessed the pump 122, videos recorded during the repair event, and physical property measurements taken during the repair event. The user interface 130 may provide the badge reader 238 for reading an identification code of the user and/or the biometric scanner 240 for obtaining biometric features of the user. The identification code of the user and/or the biometric features of the user may be received by the user interface 130 and be stored as a part of a record. The record may be linked to or associated with the user for tracking and later auditing. The record may also include time and date details to associate timing with the repair event.

In some implementations, the user interface 130 includes a display 236. The display 236 may display an alert, such as a visual alert, an audio alert, an audiovisual alert, a tactile alert, and/or the like. The alert may indicate information about the repair event, such as when the repair event is unauthorized. The audio alert, for example, may include a periodic noise or an audio file indicating the infusion system was accessed by an unauthorized user. In some implementations, the display 236 displays an indication including a banner and/or a persistent and perceivable indicator relaying information about the repair event, such as when the repair event was unauthorized.

The user interface 130 may also include a user input 234. The user input 234 may include dials, buttons, icons, selectable areas, or other perceivable indicia presented via the user interface 130 that, when interacted with (e.g., clicked, touched, selected, etc.), initiates an exchange of data for the infusion system 120 to present via the user interface 130. For example, the user input 234 may receive information about the repair event, about the user, and/or a secure value for securing the infusion system 120.

Referring again to FIG. 2, the infusion system 120 may include wired or wireless communications circuitry 226 that is connected to and/or controlled by the safety engine 110. The communication circuitry 236 may include one or more antennas (which may include a near-field communication (NFC) antenna, a Bluetooth antenna, a Bluetooth Low Energy antenna, a Wi-Fi antenna, and/or other antennas), a barcode reader, and/or a radio frequency identification (RFID) tag reader. The antenna may be configured to read from and/or write to a data tag positioned on or otherwise coupled to the infusion system 120, such as the pump 122. The data tag may be a type of wireless transceiver and may include a microcontroller unit (MCU), a memory, and an antenna (e.g., an NFC antenna) to perform the various functionalities described herein. The data tag may be, for example, a 1 Kbit or a 2 Kbit NFC tag. NFC tags with other specifications may also be used.

Additionally, and/or alternatively, the infusion system 120 may include communications circuitry 236 including one or more cellular communications features, such as via the network 105. The one or more cellular communications features may include General Packet Radio Services (GPRS), Long-Term Evolution (LTE) networks, 5G cellular technology, and/or the like. Such cellular communications features may increase system mobility and deployment options.

The communications circuitry 236 may include additional components/circuitry for other communication modes, such as, for example, NFC circuitry, Bluetooth circuitry, Bluetooth Low Energy circuitry, and/or Wi-Fi circuitry and associated circuitry (e.g., control circuitry), for communication with other devices. For example, the pump 122 may be configured to wirelessly communicate with a remote processor (e.g., the display 154, a smartphone, a tablet, wearable electronics, a cloud server, and/or the like) through the communications circuitry 236, and through this communication may receive and/or transmit one or more fluid parameters, one or more patient parameters, one or more clinician parameters, one or more fluid delivery protocols, and/or the like from and/or to one or more of the remote processors. In some implementations, based on the detection of an unauthorized repair event, the safety engine 110 may disable the communications circuitry 236. In other implementations, based on the detection of an unauthorized repair event, the safety engine 110 may cause the communications circuitry 236 to transmit information (e.g., the repair data, a timestamp, an alert, etc.) representing the repair event to a medical facility, the data system 125, and/or the like.

In some embodiments, the infusion system 120 includes a data storage 131, including one or more databases, data tables, and/or the like. The data storage 131 may store (e.g., temporarily store) the repair data, a timestamp of the repair event, a user identifier of the user accessing the infusion system, a device identifier associated with the infusion system, and/or the like. The data storage 131 may include a distributed ledger, such as a blockchain ledger.

In some implementations, one or more components of the infusion system 120, such as the replacement components of the infusion system 120 being added to the infusion system, may be scanned, such as by the infusion system 120 (e.g., the pump 122). For example, if a door or another component of the pump 122 is replaced, the repair personnel may, during the repair event, take one or more repair actions, including activating a repair mode on the pump 122, scanning the new door (or other component), making the repair, and/or verifying the repair is complete. One or more identifiers associated with the repair actions can be logged and/or written to the distributed ledger. This allows for the stored identifiers and information relating to the repair event to be evaluated later, such as during an audit. This configuration also helps to track unauthorized repair events at the pump 122. In some implementations, after and/or before the identifiers are logged to the distributed ledger, the safety engine 110 may request that the user scan and/or present authorization credentials, such as via the badge reader 238, biometrics scanner 240, and/or the like. The scanned credentials may be additionally or alternatively be stored in the distributed ledger.

Referring again to FIG. 2, the infusion system 120 includes a safety system or device 204. The safety system 204 may include at least one of a tamper switch 206, a damage switch 208, a supervisor chip 214, a tamper evident data tag 216, a light sensor 218, a camera 220, a drop sensor 222, a location sensor 224, and/or the like. The safety system 204 may be coupled to and/or form at least a part of the pump 122.

Figure 3A:
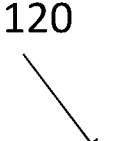
FIG. 3A depicts an example infusion system, in accordance with some example implementations.
Figure 3A:
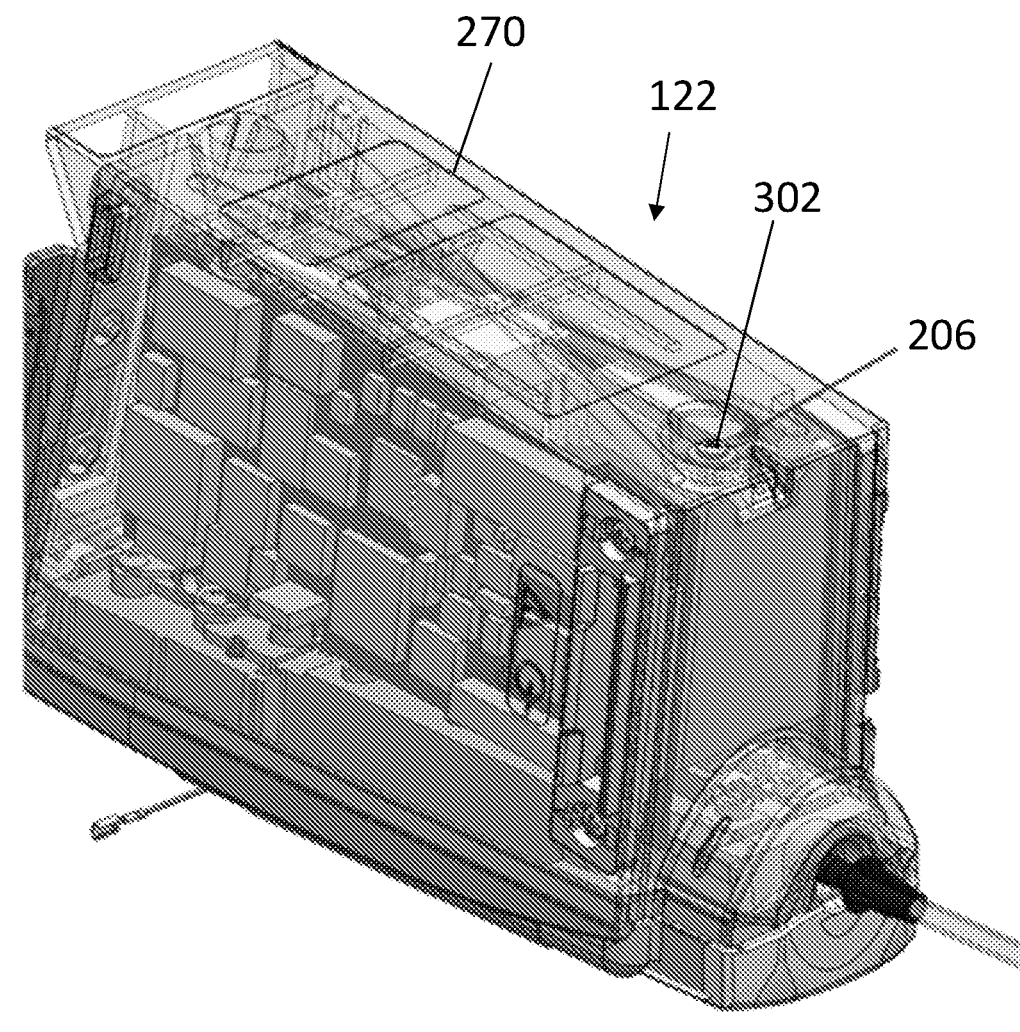
Figure 3B:
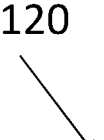
FIG. 3B depicts an example infusion system, in accordance with some example implementations.
Figure 3B:
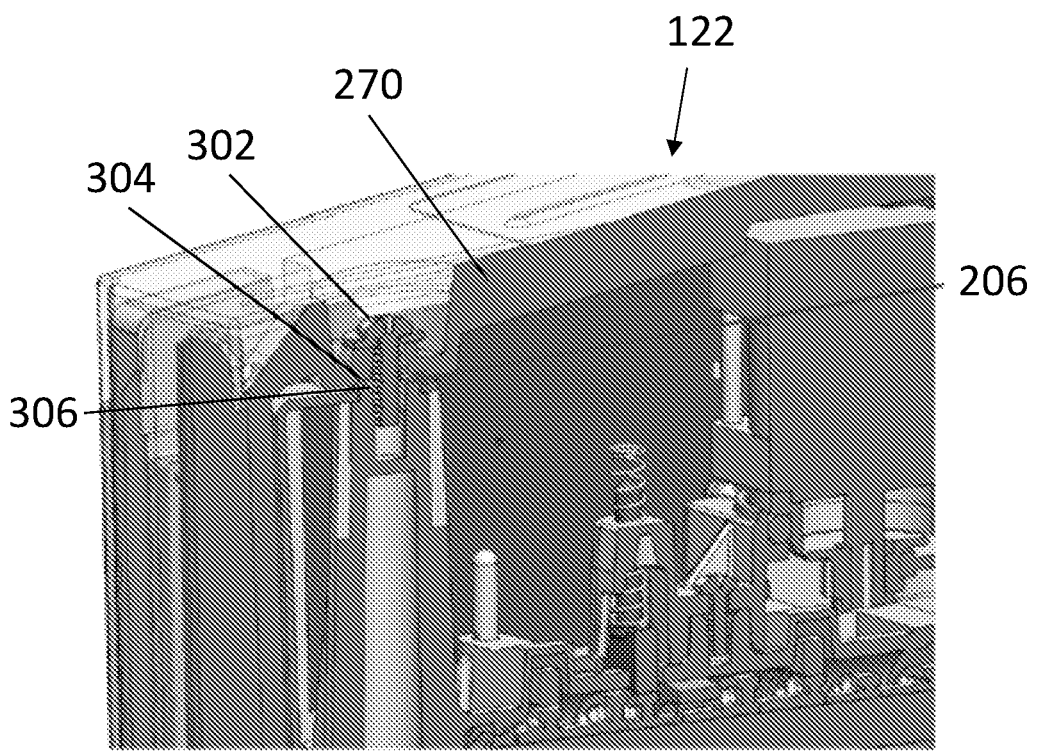

FIGS. 3A and 3B illustrate an example of the infusion system 120 including the tamper switch 206, consistent with implementations of the current subject matter. As shown in FIGS. 3A and 3B, the pump 122 includes the housing 270. The housing 270 may surround one or more internal components of the pump 122, including one or more internal structures. The housing 270 may be secured to the one or more internal structures via a fastener 302, such as a mechanical fastener (e.g., a screw), and/or the like. Loosening and/or removal of the fastener 302 may allow for removal of the housing 270 and, thus, access to the one or more internal structures of the pump 122. The fastener 302 may include one, two, three, four, five, ten or more fasteners.

The fastener 302 may maintain contact between at least two electrically conductive surfaces of the pump 122. For example, the at least two electrically conductive surfaces may include a first electrically conductive surface 304 and a second electrically conductive surface 306. In some implementations, the first electrically conductive surface 304 includes at least a portion of the housing 270 and the second electrically conductive surface 306 includes at least a portion of one of the one or more internal structures of the pump 122.

Contact between the at least two electrically conductive surfaces 304, 306 may form a circuit. For example, when the at least two electrically conductive surfaces 304, 306 are in contact with one another, the circuit may be closed. Alternatively, when the at least two electrically conductive surfaces 304, 306 are not in contact with one another, the circuit may be opened. Opening of the circuit may activate the tamper switch 206, which may include and/or be coupled to the at least two electrically conductive surfaces 304, 306, the fastener 302, and/or the housing 270.

Thus, when the fastener 302 is removed and/or loosened, such as during a repair event, the one or more internal structures of the pump 122 may be accessed, and the tamper switch 206 may be activated. In this configuration, the repair data received by the safety engine 110 may include information indicating the activation of the tamper switch. Based on the information indicating the activation of the tamper switch, the safety engine 110 may determine the repair event is unauthorized, and as a result, may cause at least one safety adjustment described herein.

Referring back to FIG. 2, the safety system 204 may include the damage switch 208. The damage switch 208 may indicate the infusion system should be accessed during a repair event, such as when the damage switch 208 detects an impact and/or damage caused to the pump 122. For example, the damage switch 208 may include a moisture sensor 210, an accelerometer 212, and/or the like.

The moisture sensor 210 may be activated upon detecting an unwanted ingress of fluid into an interior of the pump 122 and/or infusion system 120. The moisture sensor 210 may thus determine that the pump 122 has experienced fluid ingress and may need to be evaluated or repaired before being used by a patient. The moisture sensor 210 may include a film based sensor with multiple conducting lines. In some implementations, the moisture sensor 210 can include or be coupled to a circuit that includes an absorbent pad and the multiple conducting lines. When moisture enters the pump 122, the moisture may be captured on an absorbent pad. The absorbent pad capturing the moisture can close the circuit, indicating that a fault has occurred, and activating the moisture sensor (or damage switch 208). Using the moisture sensor, the repair data received by the safety engine, and from the moisture sensor, can include information indicating the activation of the moisture sensor.

The accelerometer 212 may detect an acceleration of the pump 122. For example, the accelerometer 212 can determine whether the pump 122 has been dropped and/or experiences an acceleration that exceeds a threshold acceleration, indicating a drop of the pump 122. A drop of the pump 122 may cause damage to the pump 122. Thus, the accelerometer 212 readings may indicate whether the pump 122 experienced damage or potentially experienced damage, and as a result should be evaluated. The acceleration exceeding the threshold acceleration may activate the accelerometer 212 (or damage switch 208). Using the accelerometer, the repair data received by the safety engine, and from the accelerometer, can include information indicating the activation of the accelerometer.

In some implementations, the damage switch 208 (or the tamper evident data tag 216, the light sensor 218, the camera 220, the drop sensor 222, the location sensor 224 or other safety systems) may be used in conjunction with the tamper switch 206, to detect the repair event is unauthorized. For example, the safety system 204 may include the supervisor chip 214. The supervisor chip 214 may include a processor (e.g., a microprocessor) and a memory (e.g., random access memory and/or the like). The supervisor chip 214 may help to ensure proper operation of the pump 122 and/or to detect unauthorized repair events.

For example, the supervisor chip 214 may include at least one, two, or more inputs that are connected to one or more other safety systems 204 (e.g., the tamper switch 206, the tamper evident data tag 216, the light sensor 218, the camera 220, the drop sensor 222, the location sensor 224 or other safety systems). When the supervisor chip 214 determines that one or both of the safety systems 204 coupled to the supervisor chip 214 are activated, the supervisor chip 214 may record a timestamp indicating when the safety systems 204 were activated. The timestamp may be recorded in the memory of the supervisor chip 214 and/or in the data storage 272. The timestamp can be used to later audit and/or investigate a repair event that occurred at the time the safety systems 204 were activated.

In some implementations, the supervisor chip 214 may store a security value (e.g., a numeric value, an alphanumeric value, and/or the like) in the memory of the supervisor chip 214. The security value may include a serial number of the pump 122 and/or may be otherwise associated with the pump 122. In this configuration, in order for the pump 122 to be used, the safety engine 110 may query the supervisor chip 214 for the security value. The safety engine 110 may allow use of the pump 122 when the safety engine 110 receives the security value in response to the query. When at least one, two, or more safety systems 204 are activated, the supervisor chip 214 may erase the security value from the memory of the supervisor chip 214.

In order for the pump 122 to be placed back into service, the pump 122 would need to be evaluated and/or repaired by an authorized user, who can reset the security value stored in the memory of the supervisor chip 214. For example, the safety engine 110 may detect receipt of a selection by a user via the user input 234 of an option to reset the security value and/or receipt of a new security value. The safety engine 110 may, based on the receipt of the selection and/or new security value, may cause the security value to be reset, allowing use of the infusion system or pump 122.

As an example, the safety system 204 may include a primary switch coupled to the supervisor chip 214 and a secondary switch coupled to the supervisor chip 214. The primary switch may include the tamper switch 206, or another safety system 204, and the secondary switch may include the damage switch 208, or another safety system 204. When the supervisor chip 214 receives the repair data (or an indication that one or both of the primary and secondary switches are activated) from the primary and secondary switches, the supervisor chip 214 may record a timestamp associated with the activation of the primary and secondary switches and/or erase a security value from the memory of the supervisor chip, preventing use of the infusion system or pump. Accordingly, the implementation of the supervisor chip 214 with at least one or two other safety systems 204, such as the tamper switch 206 and/or the damage switch 208, may help to track unauthorized maintenance and/or repairs of the infusion system 120, and may improve the safety of patients.

Referring again to FIG. 2, the pump 122 may include the tamper evident data tag 216. The tamper evident data tag 216 may include a smart label, an RFID tag, a holographic tag, and/or the like. The tamper evident data tag 216 may be scanned when the housing 270 is appropriately positioned on the pump 122 and the pump 122 is properly assembled. When the pump 122 is accessed, such as during a repair event, the tamper evident data tag 216 may break, leaving it unable to be scanned. In this configuration, the repair data includes the no detection of the tamper evident data tag 216 when scanned (e.g., by a scanner of the pump or receipt of a scan by the safety engine 110). The safety engine 110 may detect the repair event is unauthorized based on the no detection of the tamper evident data tag 216, and cause at least one safety adjustment described herein.

In some implementations, the pump 122 includes the light sensor (e.g., switch) 218. The light sensor 218 may be positioned within the housing 270 of the pump 122 and/or may be coupled to the pump 122 or infusion system 120. The light sensor 218 may be used to identify when the housing 270 is removed from the pump 122 during a repair event. For example, the light sensor 218 may detect darkness, indicating the presence of the housing 270. The light sensor 218 detecting light such that the amount of detected light exceeds a threshold amount indicates that the housing 270 has been removed. In some implementations, the light sensor 218 detecting the light causes the light sensor 218 and/or a switch coupled to the light sensor 218 to be thrown. When the light sensor 218 and/or switch is thrown, an indicator is written to the data storage 272. In this instance, the repair data includes a scan of a memory coupled to the light sensor and/or switch to determine whether an event indicating the light sensor and/or switch was triggered is stored in the memory. In such configurations, the safety engine 110 may perform a startup procedure during which the safety engine 110 scans the data storage 272 for the indicator. If the safety engine 110 detects the indicator, the safety engine 110 may detect an unauthorized repair event, and as a result, cause at least one safety adjustment, as described herein.

In some implementations, the pump 122 includes the camera 220. The camera 220 may capture one or more images, videos, and/or the like. The camera 220 may be coupled to the display 236. In some implementations, the safety engine 110 can determine, based on the captured images (e.g., the repair data), whether a repair event is occurring and/or whether the repair event is unauthorized. For example, the safety engine 110 may detect a repair event (e.g., an unauthorized repair event when a light level in a field of view of the camera corresponds to a light level threshold or an image shows total darkness. The light level in the field of view of the camera can indicate that the housing 270 and/or display 236 is face down on a surface or that the housing 270 is properly positioned on the pump 122 and the pump 122 is not being accessed. In some implementations, total darkness in the image can indicate that the housing 270 and/or display 236 is face down on a surface, while an image that is not total darkness can indicate that the housing 270 is properly positioned on the pump 122 and the pump 122 is not being accessed. In these configurations, the repair data may include a light level in a field of view of the camera, and the safety engine 110 detects an unauthorized repair event based on the light level corresponding to or not corresponding to a light level threshold. The safety engine 110 may as a result cause at least one safety adjustment, as described herein.

In some implementations, the pump 122 includes the drop sensor 222. The drop sensor 222 may detect a pattern of movement representing a user accessing the pump 122 and/or making a repair on the pump 122. The pattern may include an inversion or a quantity of inversion over a period of time. The safety engine 110 may receive the detected pattern, the inversion, or the quantity of inversion over the period of time (e.g., the repair data). Based on the received repair data, the safety engine may classify movement types. For example, the safety engine 110 may classify the movement type as a drop, an ambulatory transport, a repair, or another type of access of the pump 122. If the safety engine

110 determines the movement represents a repair or another type of unauthorized access, the safety engine 110 may cause at least one safety adjustment, as described herein.

In some implementations, the patient safety device maintenance system 100 may help to prevent or limit diversion of the infusion system 120 (e.g., the pump 122). For example, the infusion system 120 may be authorized and/or cleared for use in a certain location (e.g., jurisdiction). Diversion of the infusion system 120 may occur when the infusion system 120 is used in a location that is not authorized. If the infusion system 120 is used in a location that is not authorized, the safety engine 110 may determine that the use (e.g., during a repair event) of the infusion system 120 is unauthorized. As shown in FIG. 2, the safety system 204 may include the location sensor 224. The location sensor 224 may determine a location of the pump 122 based on a GPS signal, a network address, a mobile identifier of a device communicatively coupled to the pump 122, and/or the like. The safety engine 110 may receive such geofencing information as repair data, which the safety engine 110 may use to determine that the use of the pump is unauthorized. Based on the detection of the use in an unauthorized location, the safety engine 110 may cause at least one safety adjustment, as described herein.

Figure 4A:
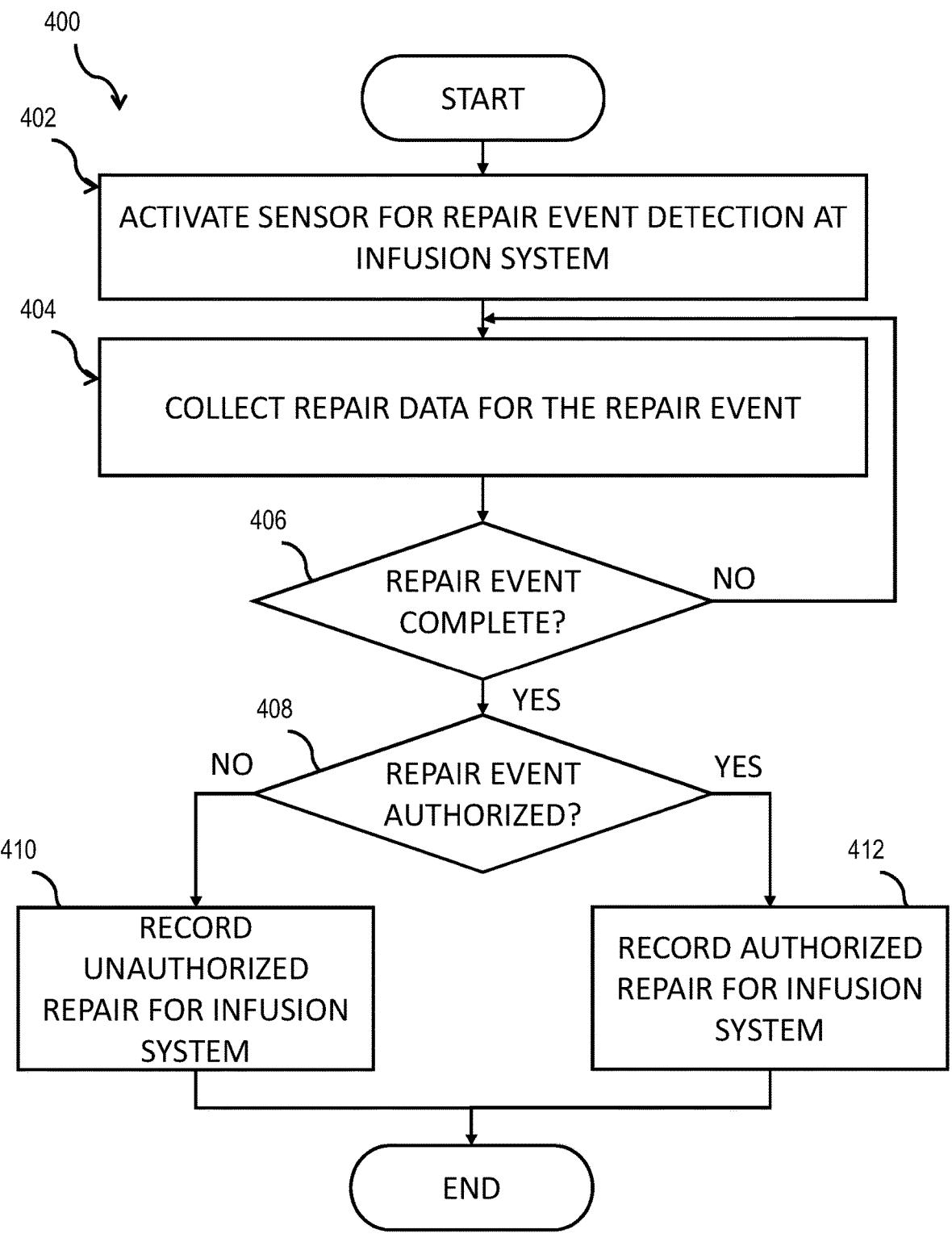
FIG. 4A depicts a flowchart illustrating a process for safe repair of an infusion device, in accordance with some example implementations.

FIG. 4A depicts a flowchart illustrating a process for safe repair of an infusion device, in accordance with some example implementations. Referring to FIG. 4A, the process 400 may be performed by the patient safety device maintenance system 100, such as by the safety engine 110 or another component of the infusion system 120 (e.g., the pump 122).

At 402, the infusion system may activate a sensor (e.g., the tamper switch 206, the damage switch 208, the supervisor chip 214, the tamper evident data tag 216, the light sensor 218, the camera 220, the drop sensor 222, the location sensor 224, or the like) to detect repair events for the infusion system. The activation may include activating the safety system 204 (e.g., one or more of the sensors, switches, accelerometers, scanners, etc. as described) to determine when the infusion system is accessed for a repair. In some implementations, the activation may be based on detecting an event such as orientation of the infusion system, a change in orientation of the infusion system, opening of a housing of the infusion system, removal of a component from the housing of the infusion system, activation of a button or other control element to indicate a repair mode, or the like.

At 404, the sensor may collect repair data for a detected repair event. The repair data may include user information for a user performing the repair, part information for a part used or replaced during the repair, or other information as described. Based at least in part on the repair data, at 406, the safety engine or the infusion system may determine whether the repair event is completed. The determination may include determining a sequence of sensor readings corresponds to a repair sequence. The determination may include assessing a measurement, such as the repair data or other measurements, of the sensor. The determination may include receiving a user input via a graphical user interface indicating the repair is complete. The determination may include detecting removal of a user token (e.g., badge of the user moving a certain distance away from the infusion system, disconnection of a user token from the infusion system, disconnection of a data path between the infusion system and a maintenance device, or the like).

Collecting the repair data may include transmitting the repair data to a safety server or other network device. In some implementations, the collection of repair data may be performed without indication to the user performing the repairs. In some implementations, it may be desirable to randomly collect repair data. In this way, a repair user may not know whether a particular repair is being monitored or not.

If the determination at 406 is negative, the process 400 may return to block 404 to collect additional repair data. Based on the repair being performed, the collection may include adjusting the sensor(s) used to collect the repair data. For example, once the housing is opened, it may not be necessary to monitor the state of a switch to detect access into the housing but rather shift to detecting, for example, battery state. In this way, the infusion system may conserve resources needed to collect and process the repair data by focusing resources on the parts or sensors related to an anticipated step in the repair process. The steps may be identified using a list or look up table where each entry identifies the particular sensor to activate and, in some implementations, a configuration of the sensor (e.g., light level threshold, load to detect, voltage threshold, target orientation, etc.).

Returning to 406, if the repair event is complete, the process 400 may proceed to 408. At 408, the safety engine or safety server (e.g., the server 126) may determine whether the repair event was authorized. The determination may be performed based on the repair data as described. If affirmative, the process 400 may moves to 412 to record authorization of the repair event. Recording may include storing a flag in a secure memory of the infusions system indicating the device is in an authorized state of repair. Recording may include submitting an entry to a distributed ledger or device registry to indicate the repair event. After recording, the process 400 may end.

Returning to 408, if the repair event is unauthorized, the process 400 at 410 may record an unauthorized repair event for the infusion system. Recording may include storing a flag in a secure memory of the infusions system indicating the device is in an unauthorized state of repair. Recording may include submitting an entry to a distributed ledger or device registry to indicate the repair event. After recording, the process 400 may end.

Figure 4B:
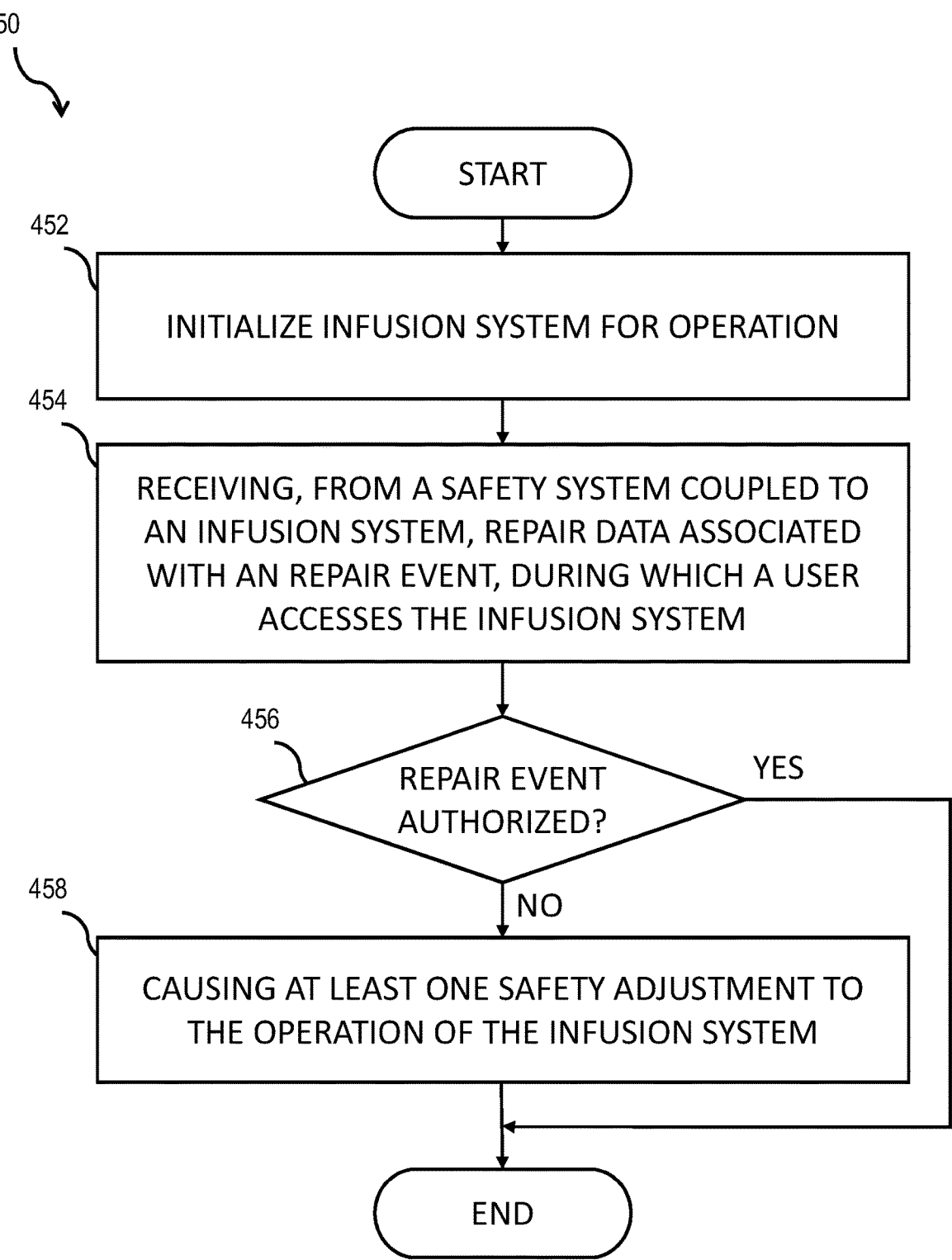
FIG. 4B depicts a flowchart illustrating a process for improving patient safety, in accordance with some example implementations.

FIG. 4B depicts a flowchart illustrating a process 450 for improving patient safety, consistent with implementations of the current subject matter. Referring to FIG. 4B, the process 450 may be performed by the patient safety device maintenance system 100, such as by the safety engine 110 or another component of the infusion system 120 (e.g., the pump 122).

At 452, the infusion system may be initiated for operation. Initiation may include adjusting the power state of the infusion system (e.g., power on, activate from stand-by, etc.). Initiation may include receiving an automated programming request to administer an infusion by the infusion system. In some implementations, initiation may include activation of a control element on a user interface of the infusion system.

At 454, the infusion system may receive repair data from the safety engine 110, or directly from the server 126, coupled to an infusion system (e.g., the infusion system 120). The repair data may be associated with a repair event, during which a user accesses the infusion system. In some implementations, the repair data may be processed by the safety engine to indicate whether the associated repair event was authorized. In some implementations, the infusion system may receive the repair data and determine authorization by processing the repair data. For example, where the repair data for the infusion system is added to a distributed ledger, the infusion system may access ledger entries associated with the infusion system. The infusion system may search the ledger based on date. For example, the infusion system may query the ledger of entries occurring after the date of the last initiation. In this way, only records that have not been reviewed are received. This can reduce the resources and time needed to determine the authorization state of the infusion system. In some implementations, the ledger may be searched using an identifier of the infusion system. This may further reduce the number of records reviewed and corresponding resources used to determine the authorization sate of the infusion system.

Consistent with implementations of the current subject matter, the repair event may include a repair of the infusion system, a maintenance performed on the infusion system, use of the infusion system, and/or the like. The repair event may be authorized or unauthorized. The repair event is authorized when the repair event is performed by an authorized user (e.g., a certified, trained, and/or qualified user). Additionally or alternatively, the repair event is authorized when an authorized component (e.g., a manufacturer approved component) is used to repair and/or replace a component of the infusion system. The repair event may be unauthorized when the repair event is performed by an unauthorized user (e.g., a user that is not certified, trained, and/or qualified). The repair event may also be unauthorized when an unauthorized component, such as a component that has not been approved by the manufacturer, is used to repair and/or replace a component of the infusion system.

The safety engine 110 may receive the repair data from the safety system. The safety system may include one or more switches, sensors, processors, and/or the like, that are used to generate repair data for use by the safety engine 110 to detect authorized and/or unauthorized access of the infusion system, such as the pump. For example, the safety system may include one or more of a tamper switch (e.g., the tamper switch 206), a damage switch (e.g., the damage switch 208), a supervisor chip (e.g., the supervisor chip 214), a tamper evident data tag (e.g., the tamper evident data tag 216), a light sensor (e.g., the light sensor 218), a camera (e.g., the camera 220), a drop sensor (e.g., the drop sensor 222), a location sensor (e.g., the location sensor 224), and/or the like. The repair data generated by the safety system may include an activation of the safety system (or an indication of the activation), captured and/or measured data including timestamps, images, acceleration data, moisture data, light data, and/or the like.

At 456, the safety engine 110 determines whether the repair event is authorized based at least in part on the repair data. For example, the safety engine 110 may compare the repair data to a threshold and detect the repair event is unauthorized based on the repair data corresponding to the threshold. The safety engine 110 may additionally or alternatively determine that the activation of one or more sensors indicates that the repair event is unauthorized. The safety engine 110 may additionally or alternatively detect the repair event is unauthorized based on the presence or absence of a security value. The safety engine 110 may additionally or alternatively detect the repair event is unauthorized based on the location of the infusion system, and/or the like. If authorized, the process 450 ends but may be repeated when the infusion system is initialized at a different time.

If unauthorized, the process 450 may move to 458. At 458, the safety engine 110 causes at least one safety adjustment to operation of the infusion system based on the detection that the repair event is unauthorized. Additionally or alternatively, the safety engine 110 causes at least one safety adjustment based on detection of a repair event. The at least one safety adjustment may include transmission of an alert, storage of information associated with the repair event, transmission of an alarm, disablement of the infusion system, changing an operation of the infusion system, and/or the like. Thus, the safety engine 110 may track access of the infusion system for later auditing and/or investigation, and in some instances, may prevent use of the infusion system until the infusion system 120 is evaluated by an authorized user. Accordingly, the safety engine 110 may improve patient safety and allow for tracking of repair events, including unauthorized repair events.

Figure 5:
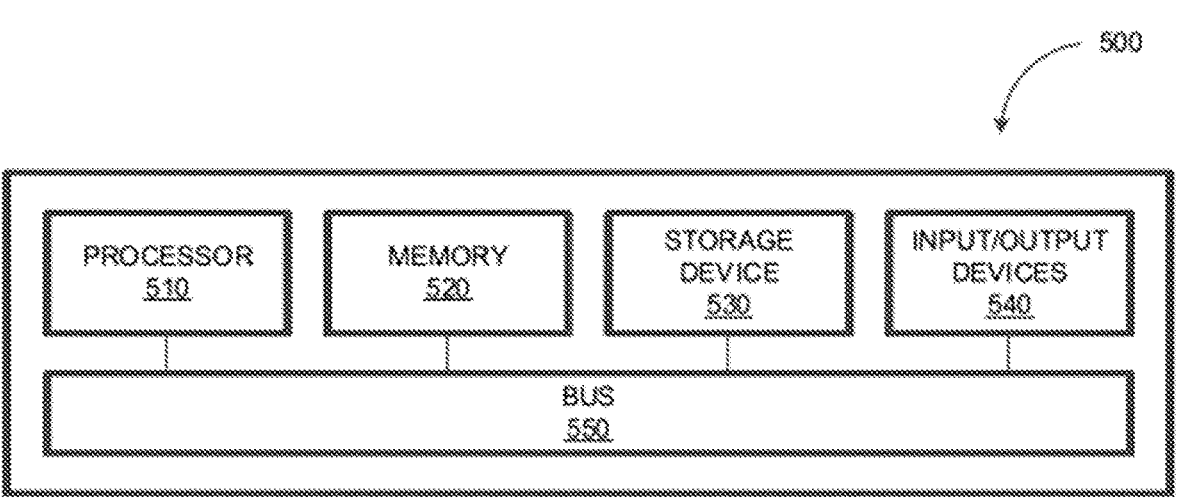
FIG. 5 depicts a block diagram illustrating a computing system, in accordance with some example implementations.

FIG. 5 depicts a block diagram illustrating a computing system 500 consistent with implementations of the current subject matter. Referring to FIGS. 1 and 5, the computing system 500 can be used to implement the patient safety device maintenance system 100, the pump 122, the safety engine 110 and/or any components therein.

As shown in FIG. 5, the computing system 500 can include a processor 510, a memory 520, a storage device 530, and input/output devices 540. The processor 510, the memory 520, the storage device 530, and the input/output devices 540 can be interconnected via a system bus 550. The processor 510 is capable of processing instructions for execution within the computing system 500. Such executed instructions can implement one or more components of, for example, the safety engine 110. In some example implementations, the processor 510 can be a single-threaded processor. Alternatively, the processor 510 can be a multi-threaded processor. The processor 510 is capable of processing instructions stored in the memory 520 and/or on the storage device 530 to present graphical information for a user interface provided via the input/output device 540.

The memory 520 is a computer readable medium such as volatile or non-volatile that stores information within the computing system 500. The memory 520 can store data structures representing configuration object databases, for example. The storage device 530 is capable of providing persistent storage for the computing system 500. The storage device 530 can be a floppy disk device, a hard disk device, an optical disk device, or a tape device, or other suitable persistent storage means. The input/output device 540 provides input/output operations for the computing system 500. In some example implementations, the input/output device 540 includes a keyboard and/or pointing device. In various implementations, the input/output device 540 includes a display unit for displaying graphical user interfaces.

According to some example implementations, the input/output device 540 can provide input/output operations for a network device. For example, the input/output device 540 can include Ethernet ports or other networking ports to communicate with one or more wired and/or wireless networks (e.g., a local area network (LAN), a wide area network (WAN), the Internet).

In some example implementations, the computing system 500 can be used to execute various interactive computer software applications that can be used for organization, analysis and/or storage of data in various formats. Alternatively, the computing system 500 can be used to execute software applications. These applications can be used to perform various functionalities, e.g., planning functionalities (e.g., generating, managing, editing of spreadsheet documents, word processing documents, and/or any other objects, etc.), computing functionalities, communications functionalities, etc. The applications can include various add-in functionalities or can be standalone computing products and/or functionalities. Upon activation within the applications, the functionalities can be used to generate the user interface provided via the input/output device 540. The user interface can be generated and presented to a user by the computing system 500 (e.g., on a computer screen monitor, etc.).

Figure 6A:
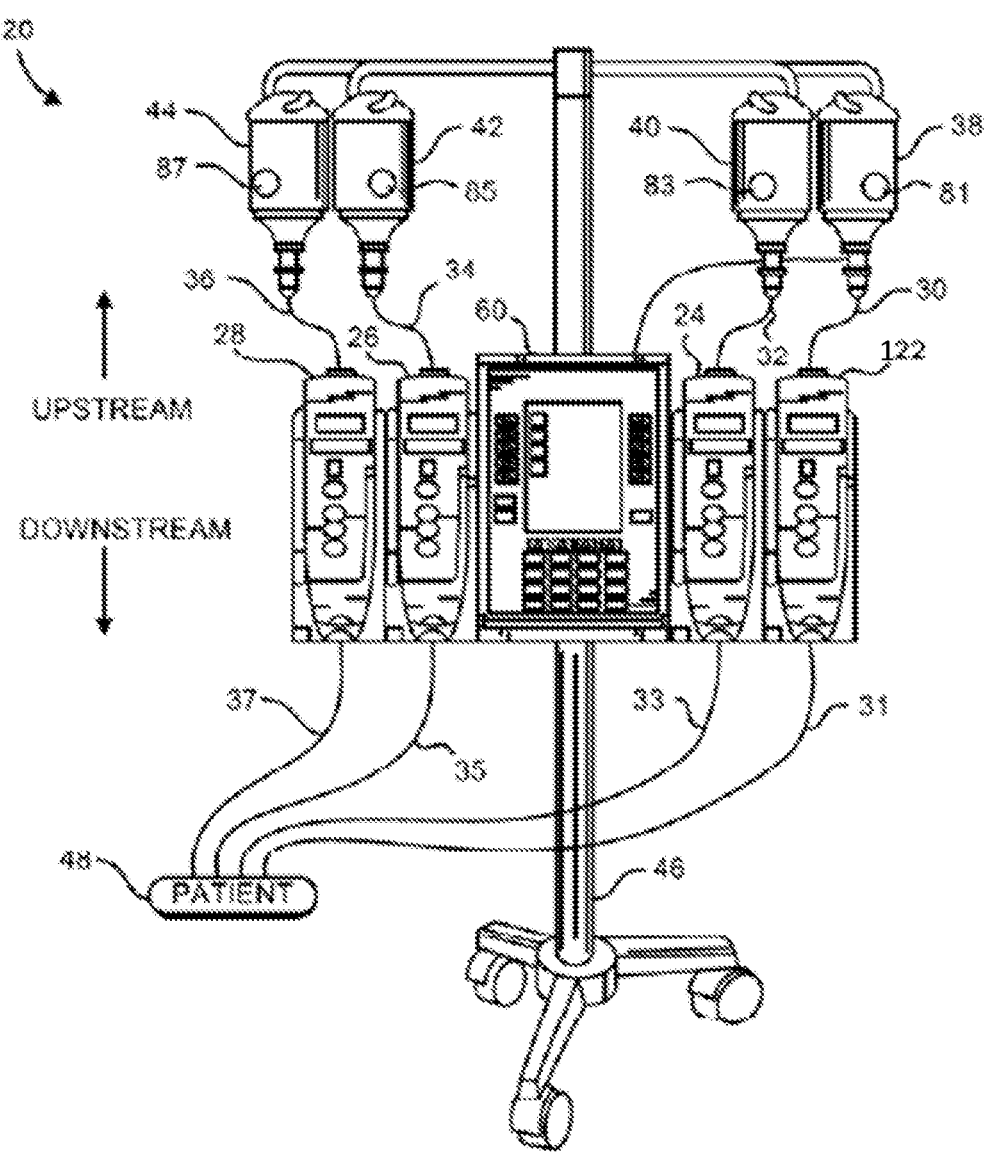
FIG. 6A depicts a front view of a patient care system, in accordance with some example implementations.
Figure 6B:
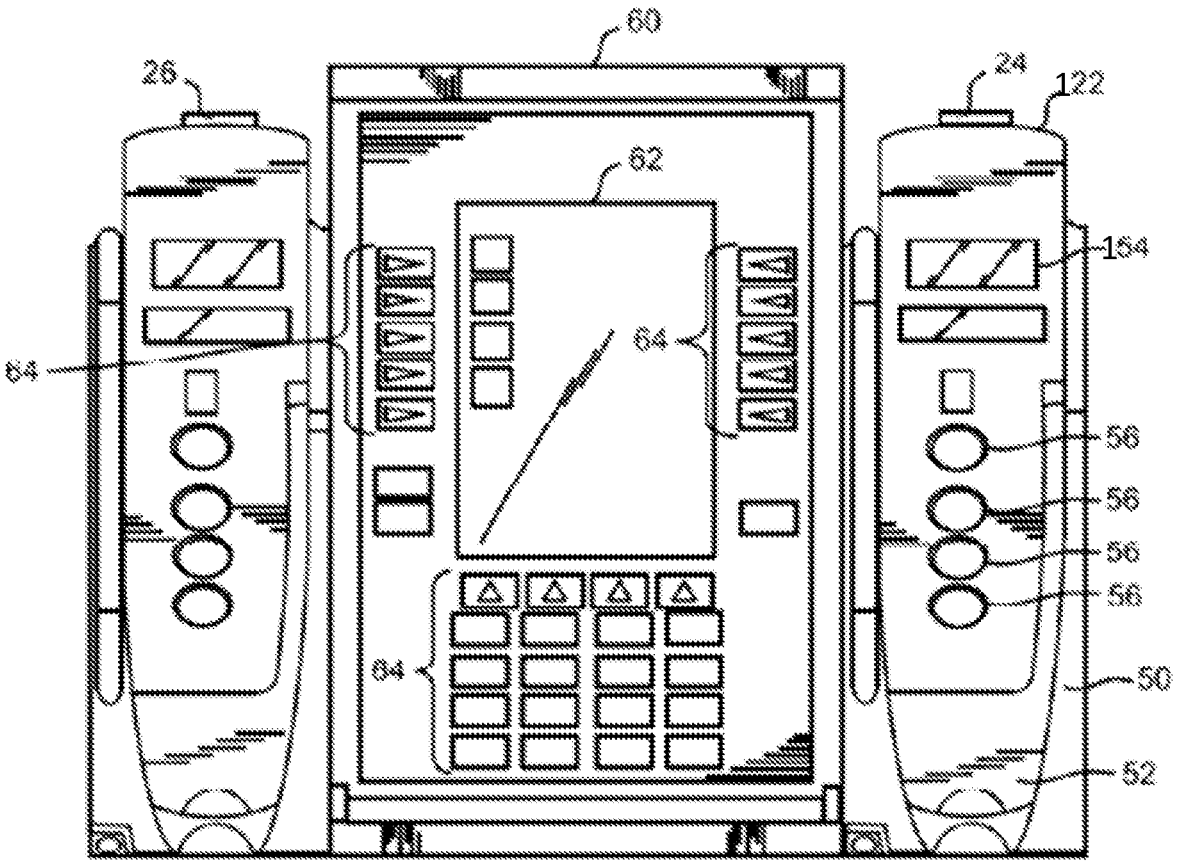
FIG. 6B depicts an enlarged view of a portion of a patient care system, in accordance with some example implementations.
Figure 6C:
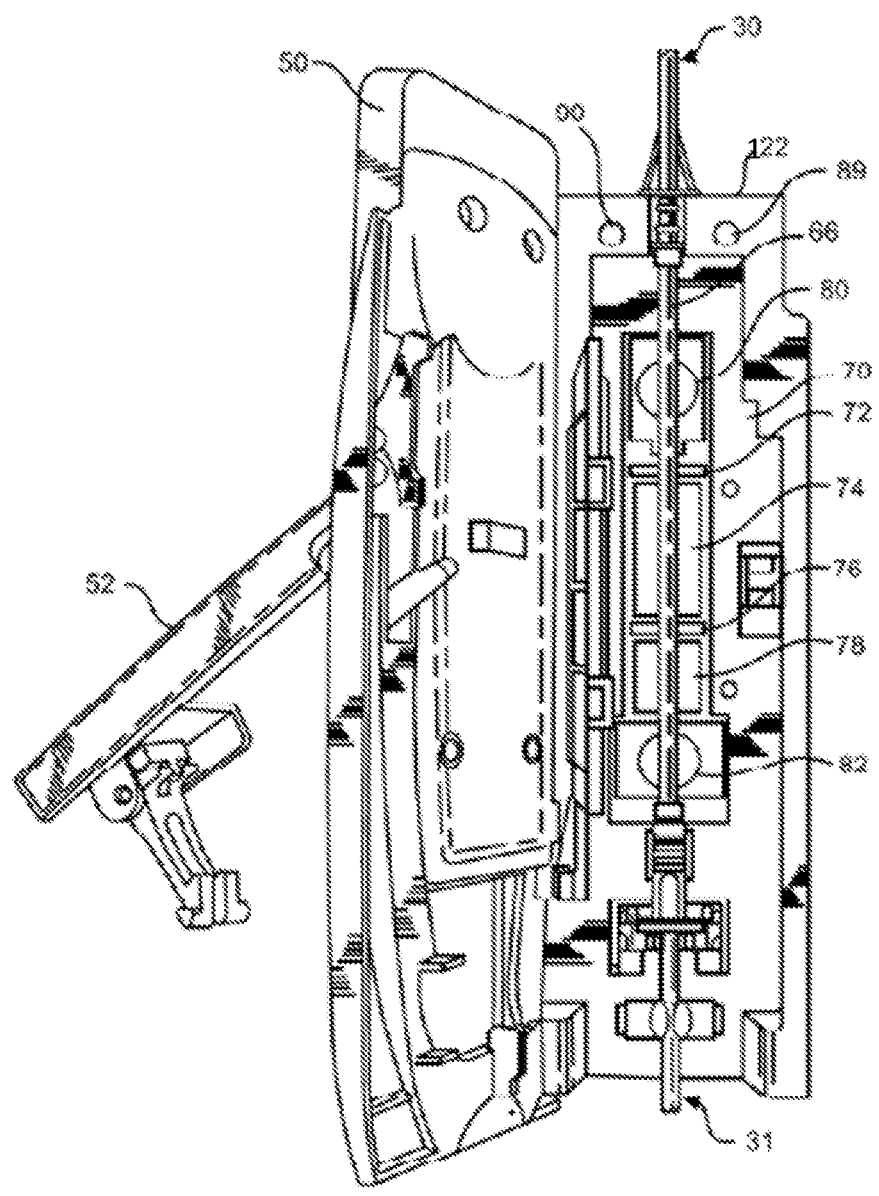
FIG. 6C depicts a perspective view of a pump, in accordance with some example implementations.

In some example implementations, the pump 122 may be part of a patient care system 20. FIGS. 6A-6C illustrate example implementations of the patient care system 20, though other types of patient care systems may be implemented. Referring to FIG. 6A, the patient care system 20 may include the pump 122 as well as additional pumps 24, 26, and 28. Although a large volume pump (LVP) is illustrated, other types of pumps may be implemented, such as a small volume pump (SVP), a TCI pump, a syringe pump, an anesthesia delivery pump, and/or a patient-controlled analgesic (PCA) pump configured to deliver a medication (e.g., an anesthesia, such as propofol and/or remifentanil, and the like) to a patient. The pump 122 may be any infusion device configured to deliver a substance (e.g., fluid, nutrients, medication, and/or the like) to a patient's circulatory system or epidural space via, for example, intravenous infusion, subcutaneous infusion, arterial infusion, epidural infusion, and/or the like, or the pump 122 may be an infusion device configured to deliver a substance (e.g., fluid, nutrients, medication, and/or the like) to a patient's digestive system via a nasogastric tube (NG), a percutaneous endoscopic gastrostomy tube (PEG), nasojejunal tube (NJ), and/or the like.

As shown in FIG. 6A, each of the pump 122, 24, 26, and 28 may be fluidly connected with an upstream fluid line 30, 32, 34, and 36, respectively. Moreover, each of the four pumps 122, 24, 26, and 28 may also fluidly connected with a downstream fluid line 31, 33, 35, and 37, respectively. The fluid lines can be any type of fluid conduit, such as tubing, through which fluid can flow. At least a portion of one or more of the fluid lines may be constructed with a multi-layered configuration as described herein.

Fluid supplies 38, 40, 42, and 44, which may take various forms but in this case are shown as bottles, are inverted and suspended above the pumps. Fluid supplies may also take the form of bags, syringes, or other types of containers. Both the patient care system 20 and the fluid supplies 38, 40, 42, and 44 may be mounted to a roller stand or intravenous (IV) pole 46.

A separate pump 122, 24, 26, and 28 may be used to infuse each of the fluids of the fluid supplies into the patient. The pumps 122, 24, 26, and 28 may be flow control devices that will act on the respective fluid line to move the fluid from the fluid supply through the fluid line to the patient 48. Because individual pumps are used, each can be individually set to the pumping or operating parameters required for infusing the particular medical fluid from the respective fluid supply into the patient at the particular rate prescribed for that fluid by the physician. Such medical fluids may comprise drugs or nutrients or other fluids.

Typically, medical fluid administration sets have more parts than are shown in FIG. 6A. Many have check valves, drip chambers, valved ports, connectors, and other devices well known to those skilled in the art. These other devices have not been included in the drawings so as to preserve clarity of illustration. In addition, it should be noted that the drawing of FIG. 6A is not to scale and that distances have been compressed for the purpose of clarity. In an actual setting, the distance between the bottles 38, 40, 42, and 44 and the pump modules 22, 24, 26, and 28 could be much greater.

Referring now to FIG. 6B, an enlarged view of the front of the patient care system 20 is shown. The pump 122 may include a front door 50 and a handle 52 that operates to lock the door in a closed position for operation and to unlock and open the door for access to the internal pumping and sensing mechanisms and to load administration sets for the pump. In some implementations, the safety engine 110 determines when the door, the handle, and/or other components of the pump 122 are accessed, replaced, and/or repaired. When the door is open, the tube can be connected with the pump, as will be shown in FIG. 6C. When the door is closed, the tube is brought into operating engagement with the pumping mechanism, the upstream and downstream pressure sensors, and the other equipment of the pump. A display 154, such as an LED display, is located in plain view on the door in this embodiment and may be used to visually communicate various information relevant to the pump, such as alert indications (e.g., alarm messages). For example, the display 154 may display one or more alerts and/or indications indicating access, such as authorized and/or unauthorized access of the infusion system. The display 154 may otherwise be a part of or be coupled to the pump 122. Control keys 56 exist for programming and controlling operations of the pump as desired. The pump 122 also includes audio alarm equipment in the form of a speaker (not shown).

In the embodiment shown, a programming module 60 is attached to the left side of the pump 122. In some implementations, the programming module 60 forms a part of the pump 122. Other devices or modules, including another pump, may be attached to the right side of the pump 122, as shown in FIG. 6A. In such a system, each attached pump represents a pump channel of the overall patient care system 20. In one embodiment, the programming module is used to provide an interface between the pump 122 and external devices as well as to provide most of the operator interface for the pump 122.

The programming module 60 includes a display 62 for visually communicating various information, such as the operating parameters of the pump 122 and alert indications and alarm messages. The programming module 60 may also include a speaker to provide audible alarms. The programming module or any other module also has various input devices in this embodiment, including control keys 64 and a bar code or other scanner or reader for scanning information from an electronic data tag relating to the infusion, the patient, the care giver, or other. The programming module also has a communications system (not shown) with which it may communicate with external equipment such as a medical facility server or other computer and with a portable processor, such as a handheld portable digital assistant ("PDA), or a laptop-type of computer, or other information device that a care giver may have to transfer information as well as to download drug libraries to a programming module or pump. In some implementations, the programming module 60 may communicate with the safety engine 110, include the safety engine 110, or implement features of the safety engine 110 described herein.

The communications system may take the form of a radio frequency ("RF") (radio frequency) system, an optical system such as infrared, a Blue Tooth system, or other wired or wireless system. The bar code scanner and communications system may alternatively be included integrally with the pump 122, such as in cases where a programming module is not used, or in addition to one with the programming module. Further, information input devices need not be hard-wired to medical instruments, information may be transferred through a wireless connection as well.

FIG. 6B includes a second pump 26 connected to the programming module 60. As shown in FIG. 6A, more pump modules may be connected. Additionally, other types of modules may be connected to the pump modules or to the programming module.

Turning now to FIG. 6C, the pump 122 is shown in perspective view with the front door 50 open, showing the upstream fluid line 30 and downstream fluid line 31 in operative engagement with the pump 122. The pump 122 directly acts on a tube 66 (also referred to as a pump segment) that connects the upstream fluid line 30 to the downstream fluid line 31 to form a continuous fluid conduit, extending from the respective fluid supply 38 (FIG. 6A) to the patient 48, through which fluid is acted upon by the pump to move fluid downstream to the patient. Specifically, a pumping mechanism 70 acts as the flow control device of the pump to move fluid though the conduit. The upstream and downstream fluid lines and/or tube 66 may be coupled to a pump cassette or cartridge that is configured to be coupled to the pump 122, such as the type described in co-pending U.S. patent application Ser. No. 13/827,775, which is incorporated by reference herein.

The type of pumping mechanism may vary and may be for example, a multiple finger pumping mechanism. For example, the pumping mechanism may be of the "four finger" type and includes an upstream occluding finger 72, a primary pumping finger 74, a downstream occluding finger 76, and a secondary pumping finger 78. The "four finger" pumping mechanism and mechanisms used in other linear peristaltic pumps operate by sequentially pressing on a segment of the fluid conduit by means of the cam-following pumping fingers and valve fingers 72, 74, 76, and 78. The pressure is applied in sequential locations of the conduit, beginning at the upstream end of the pumping mechanism and working toward the downstream end. At least one finger is always pressing hard enough to occlude the conduit. As a practical matter, one finger does not retract from occluding the tubing until the next one in sequence has already occluded the tubing; thus at no time is there a direct fluid path from the fluid supply to the patient. The operation of peristaltic pumps including four finger pumps is well known to those skilled in the art and no further operational details are provided here.

In this particular embodiment, FIG. 6C further shows a downstream pressure sensor 82 included in the pump 122 at a downstream location with respect to the pumping mechanism. The downstream pressure sensor 82 is mounted to the flow control device 70 and is located adjacent and downstream in relation to the flow control device. The downstream pressure sensor is located downstream from the flow control device, that is, at a location between the patient 48 (FIG. 6A) and the flow control device, so that the connection of the correct fluid supply with the correct pump may be verified before any fluid is pumped to the patient.

With reference still to FIG. 6C, an upstream pressure sensor 80 may also be included in the pump 122. The upstream pressure sensor is assigned to the flow control device or pumping mechanism 70 and, in this embodiment, is further provided as an integral part of the pump 122. It is mounted to the flow control device 70 and is located adjacent and upstream in relation to the flow control device. The upstream pressure sensor is located upstream from the flow control device, that is, at a location between the fluid supply 38 (FIG. 6A) and the flow control device, so that the connection of the correct fluid supply with the correct pump may be verified before any fluid is pumped to the patient. In an implementation where the source is a syringe, the flow control device 70 may be configured to press a plunger of the syringe to provide the infusion according to the programmed parameters.

Figure 7:
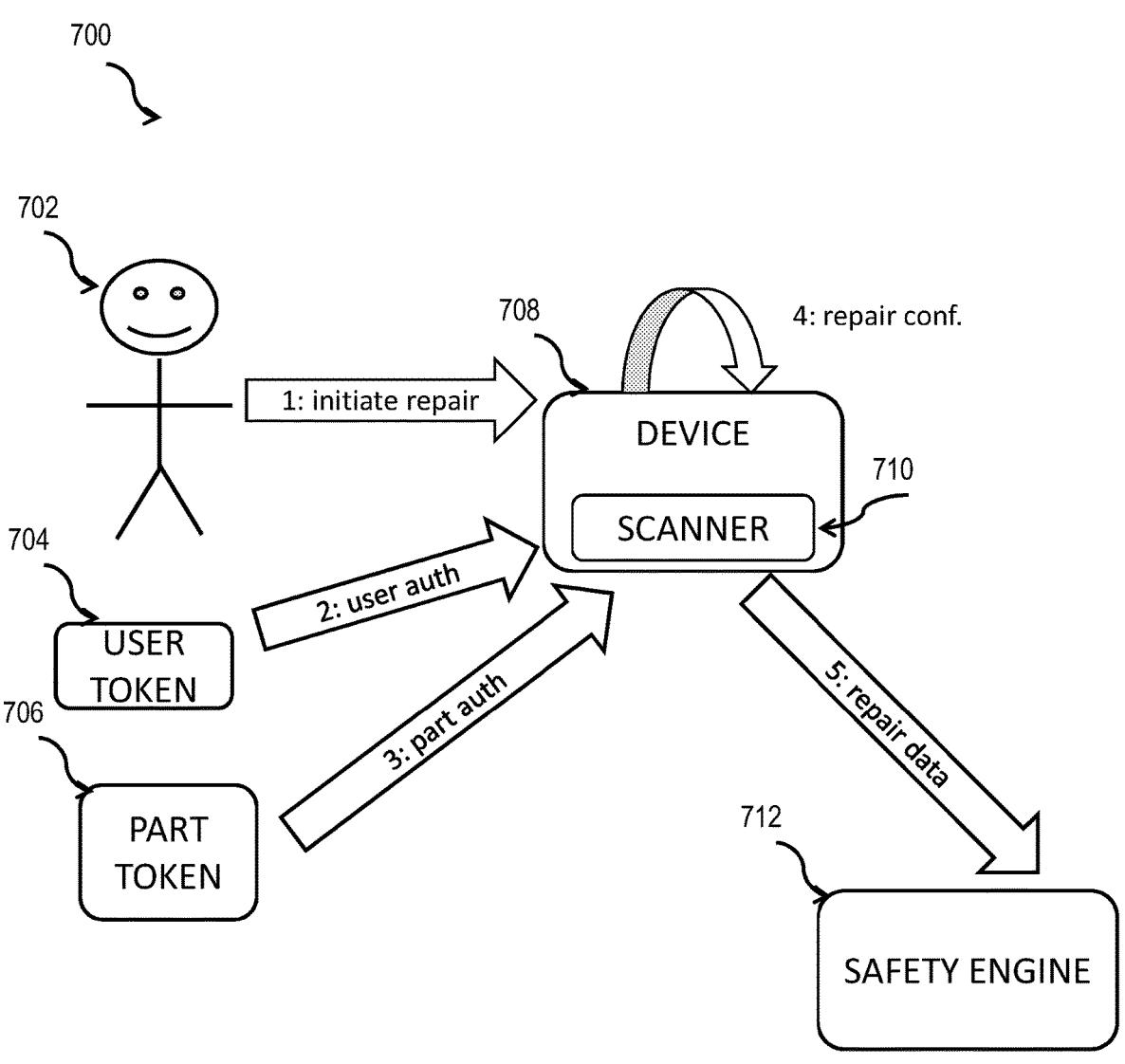
FIG. 7 depicts a process diagram for secure repair of a device, in accordance with some example implementations.

FIG. 7 depicts a process diagram for secure repair of a device, in accordance with some example implementations. The process 700 may include a user 702 to repair a device 708, which may be and/or include the infusion system 120. The user 702 may initiate repair (e.g., a repair event). Initiating repair may include activating a user interface element of the device 708. Initiating repair may include opening the housing of the device 708. Initiating repair may include virtually accessing firmware or other software stored in memory of the device 708.

After initiating repair, the user 702 may provide a user token 704 to the device 708. As shown in FIG. 7, the device 708 may include a scanner 710. The scanner 710 may be activated to receive the user token 704. The user token 704 may be a wireless contact card including information that can be read by the scanner 710. The user token 704 may include biometric information such as a fingerprint, facial recognition, iris scan, or the like. In some implementations, the user token 704 may be stored in a storage device such as a removable storage drive that can be connected to the device 708. The user authorization via the user token 704 allows the system to associate activities and associated repair data at the device 708 with the user 702 associated with the user token 704.

In some implementations, the user 702 may repair, replace, update, or clean a part of the device 708. The user 702 may scan the new part using the scanner 710. The user 702 may additionally or alternatively scan the old part using the scanner 710. In this way, a record of the part(s) included in the device 708 may be recorded as described herein (e.g., blockchain, database, distributed ledger, etc.).

The device 708 may confirm that the repair is performed or completed. The confirmation may include determining the housing is secured or receiving a completion indication via a user interface. In some implementations, the scanner 710 may activate after the housing is secure to take an inventory of parts within the housing of the device 708. This inventory information may be included in the repair data associated with the repair event.

The device 708 may transmit the repair data to a safety engine 712. The transmission may include an identifier for the device 708 such as a media access control identifier, network address, serial number, or other information to uniquely identify the device 708. The safety engine 712 may store the repair data in a data store, such as at a server. In some implementations, the safety engine 712 may process the repair data to assess the repair data to determine whether the repair is authorized or unauthorized. The assessment may be performed in real-time, during the repair event. As used herein, "real-time" may refer to availability for processing at or near in time to the time the associated repair data is generated or detected. In some implementations, the assessment may be performed after the repair event is complete. For example, when the device 708 is powered on after the repair event, the initialization of the device 708 may include communication with the safety engine 712 to determine whether the device 708 was improperly repaired. As discussed, in some implementations, the safety engine 712 may be included in the device 708.

Figure 8:
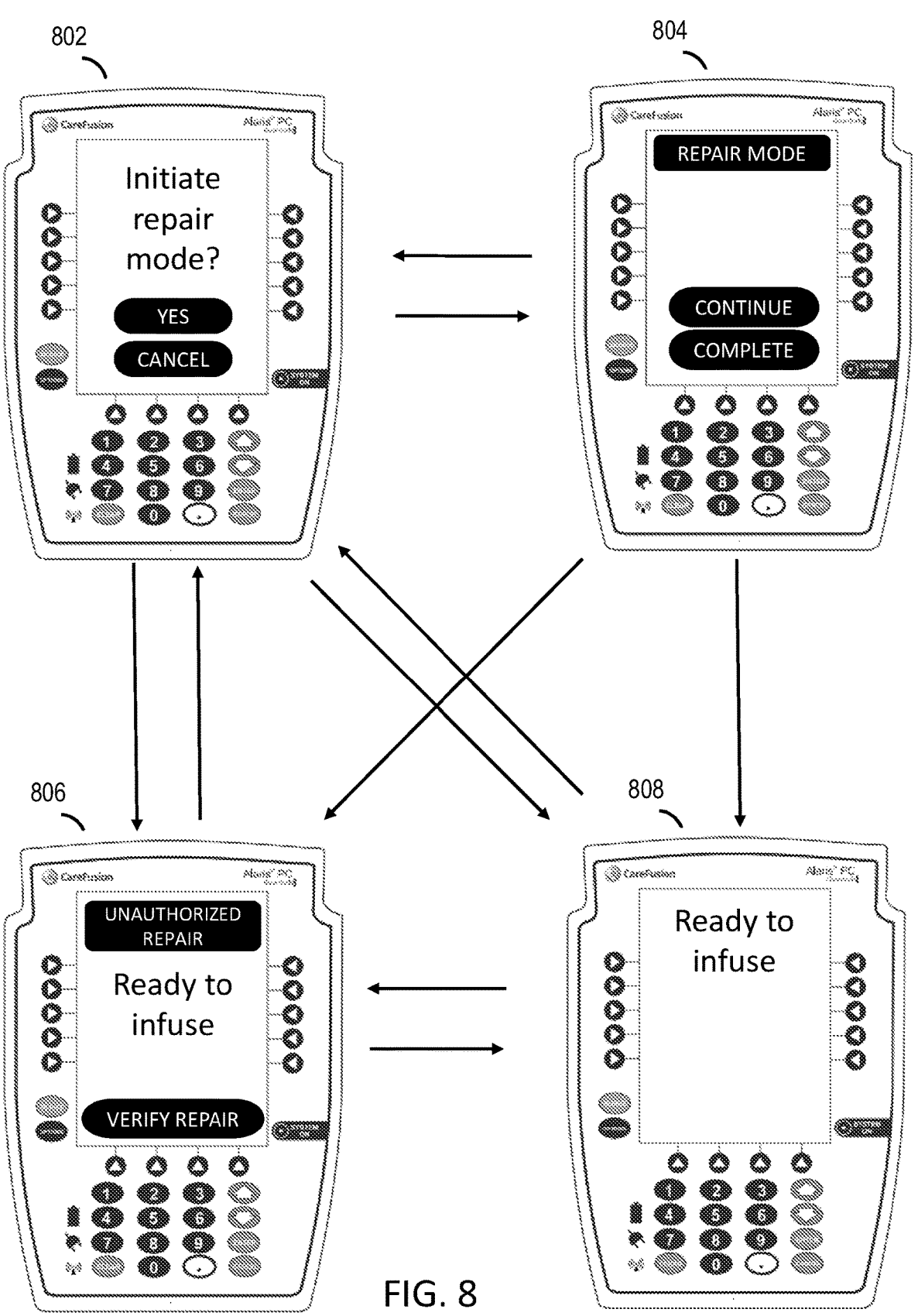
FIG. 8 depicts a state diagram of user interfaces for improving patient safety when using a repaired infusion device, in accordance with some example implementations.

FIG. 8 depicts a state diagram of user interfaces for improving patient safety when using a repaired infusion device, in accordance with some example implementations. At state 808, the device may indicate a readiness to infuse. From state 808, the device may be explicitly activated to enter a repair mode, state 802. The activation may include selecting a control element on a user interface or pressing a specific button or sequence of buttons to enter a maintenance/repair mode. Once in state 802, the device may return to state 808 if the user cancels the repair mode. Cancelling the repair mode without making any changes may be desirable when the repair mode is accidentally initiated or detected (e.g., based on orientation, location, etc.). However, if the repair mode is confirmed (e.g., selecting the YES button), the device may transition to state 804. At state 804, an indication of the state of the device as being in "repair mode" may be provided. The indication may be provided, for example, as a static element on the user interface of the device, such as shown in FIG. 8. Other manifestations may include activating a light, sound, or other human perceivable indication of the repair state.

From state 804, a user may continue repairing the device. The continue control element may be presented in implementations where the user performs a series of steps to make the repair such as opening the housing, scanning a new part, etc. If the repair is continued, the device may remain in state 804. However, if the repair is marked complete, the device may move to either state 806 or state 808 depending on whether the repair event was authorized.

To move to state 808, the security engine may process the repair event and associated repair data to determine whether the repair was authorized. Authorization may include confirming, via the safety engine as described, the permissions of the user associated with the repair, the parts used during the repair, the order of steps performed for the repair, the operational status of the device after the repair, or the like as derived from the repair data and/or device data (e.g., self-test, switch state, value stored at a secured memory location, etc.). If the repair event was authorized, the device may transition to state 808. From state 808, the device may be operated with confidence that the repaired state was performed safely. From state 808, the device may transition to state 802 to perform another repair as described.

However, from state 804, if the repair event was unauthorized, the device may transition to state 806. In the example shown in FIG. 8, the user interface may present a perceivable indicator that the device was repaired in an unauthorized fashion. The indication may be provided, for example, as a static element on the user interface of the device, such as shown in FIG. 8. Other manifestations may include activating a light, sound, or other human perceivable indication of the repair state.

As shown in FIG. 8, the device in state 806 may provide some infusion functionality. For example, the device may disable network connectivity to prevent malicious or unsecured software from the clinical network. However, the device may still be accessed and used to provide treatment to a patient. In some implementations, the device at state 806 may provide an option to verify an unauthorized repair. As shown, the user interface of the device may include a control element (e.g., button) to verify the repair. Once activated, the device may require one or more input values to allow an authorized user to confirm the repair and return the device to the authorized state 808. The confirmation may include receiving a user token or other credential to "sign-off" on the device.

In some implementations, the device may include two or more repair events. In such instances, one repair event may be authorized while a second repair event may be unauthorized. While in the unauthorized state 806, the device may be operated to return to state 802 to perform an additional repair. If the additional repair is not performed (e.g., cancelled) the device will return to the unauthorized state 806.

One or more aspects or features of the subject matter described herein can be realized in digital electronic circuitry, integrated circuitry, specially designed ASICs, field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive track pads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

As used herein a "user interface" (also referred to as an interactive user interface, a graphical user interface or a UI) may refer to a network based interface including data fields and/or other control elements for receiving input signals or providing electronic information and/or for providing information to the user in response to any received input signals. Control elements may include dials, buttons, icons, selectable areas, or other perceivable indicia presented via the UI that, when interacted with (e.g., clicked, touched, selected, etc.), initiates an exchange of data for the device presenting the UI. A UI may be implemented in whole or in part using technologies such as hyper-text mark-up language (HTML), FLASH™, JAVA™, .NET™, web services, or rich site summary (RSS). In some implementations, a UI may be included in a stand-alone client (for example, thick client, fat client) configured to communicate (e.g., send or receive data) in accordance with one or more of the aspects described. The communication may be to or from a medical device or server in communication therewith.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A system, comprising:

at least one data processor; and at least one memory storing instructions which, when executed by the at least one data processor, result in operations comprising:

receiving, from a safety system coupled to an infusion system, repair data associated with a repair event, during which an element within a housing of the infusion system is accessed, wherein the safety system comprises a supervisor chip coupled to the infusion system, a primary switch coupled to the supervisor chip and to the infusion system, and a secondary switch coupled to the supervisor chip and to the infusion system;

detecting, based on the repair data, the repair event is unauthorized; and causing, based on the detecting, at least one safety adjustment to operation of the infusion system, wherein the at least one safety adjustment comprises erasing a security value from memory of the supervisor chip, thereby limiting use of the infusion system.

2. The system of claim 1, wherein the repair event comprises one or more of a repair of the element of the infusion system, a replacement of the element of the infusion system, opening the housing, and a maintenance performed on the infusion system.

3. The system of claim 1, wherein the infusion system comprises an infusion pump.

4. The system of claim 1, wherein the infusion system comprises: an infusion pump; and a control device coupled to the infusion pump, the control device comprising at least one data processor and at least one memory storing instructions which, when executed by the at least one data processor, control operation of the infusion pump.

5. The system of claim 1, wherein the safety system comprises a tamper switch, the tamper switch comprising:

at least two electrically conductive surfaces of the infusion system; wherein contact between the at least two electrically conductive surfaces forms a circuit; and a fastener configured to maintain contact between the at least two electrically conductive surfaces;

wherein removal of the fastener is configured to allow access to the infusion system during the repair event; and wherein the removal of the fastener is further configured to activate the tamper switch.

6. The system of claim 5, wherein the safety system further comprises the housing of the infusion system, the housing defining at least one of the at least two electrically conductive surfaces.

7. The system of claim 6, wherein the repair data comprises information indicating activation of the tamper switch; and wherein the detecting comprises determining the repair event is unauthorized when the tamper switch is activated.

8. The system of claim 1, wherein the safety system comprises a damage switch configured to indicate the infusion system should be accessed during the repair event, wherein the damage switch comprises one or more of a moisture sensor configured to be activated upon detecting an ingress of fluid into an interior of the infusion system and an accelerometer configured to be activated upon detecting an acceleration indicating an impact on the infusion system.

9. The system of claim 1, wherein the repair data comprises information indicating activation of one or more of the primary switch and the secondary switch.

10. The system of claim 9, wherein the at least one safety adjustment comprises recording, by the supervisor chip, a timestamp associated with the activation of the one or more of the primary switch and the secondary switch.

11. The system of claim 1, wherein the operations further comprise: resetting the security value upon receipt of a selection from an authorized user, thereby restoring the use of the infusion system.

12. The system of claim 1, wherein the safety system comprises a light sensor and/or switch within a housing of the infusion system; wherein the repair data comprises a scan of a memory coupled to the light sensor and/or switch to determine whether an event indicating the light sensor and/or switch was triggered is stored in the memory, the light sensor and/or switch being triggered when the housing is removed from the infusion system; and wherein the detecting comprises determining the repair event is unauthorized based on a determination that the event is stored in the memory.

13. The system of claim 1, wherein the safety system comprises a camera coupled to the housing of the infusion system; wherein the repair data comprises a light level in a field of view of the camera; and wherein the detecting comprises determining the repair event is unauthorized based on the light level in the field of view of the camera corresponding to a light level threshold.

14. The system of claim 1, further comprising an authorized user registry; and wherein the repair data includes user data associated with the infusion system during the repair event, and wherein determining the repair event is unauthorized includes determining that the user data is unassociated with a user included in the authorized user registry.

15. The system of claim 1, further comprising an authorized user registry; and wherein the repair data includes user data associated with the infusion system during the repair event, and wherein determining the repair event is unauthorized includes determining that the user data is associated with a user authorized to perform a different repair event than the repair event in the authorized user registry.

16. The system of claim 1, wherein the at least one safety adjustment comprises creation, in a distributed ledger, of an entry comprising an identifier associated with the infusion system and a timestamp of the repair event.

17. The system of claim 16, wherein the distributed ledger is a blockchain ledger.

18. A method, comprising:

receiving, from a safety system coupled to an infusion system, repair data associated with a repair event, during which an element within a housing of the infusion system is accessed, wherein the safety system comprises a supervisor chip coupled to the infusion system, a primary switch coupled to the supervisor chip and to the infusion system, and a secondary switch coupled to the supervisor chip and to the infusion system;

detecting, based on the repair data, the repair event is unauthorized; and causing, based on the detecting, at least one safety adjustment to operation of the infusion system, wherein the at least one safety adjustment comprises erasing a security value from memory of the supervisor chip, thereby limiting use of the infusion system.

19. The method of claim 18, wherein the repair event comprises one or more of a repair of the element of the infusion system, a replacement of the element of the infusion system, opening the housing, and a maintenance performed on the infusion system.

20. The method of claim 18, wherein the repair data includes user data associated with the infusion system during the repair event, and wherein determining the repair event is unauthorized includes determining that the user data is unassociated with a user included in an authorized user registry.

* * * * *